US012653613B2

(12) United States Patent
Shroff et al.

(10) Patent No.:  US 12,653,613 B2
(45) Date of Patent:  *Jun. 16, 2026

(54) METHODS AND DEVICES FOR GENERATING AND DELIVERING SHAPED MICROWAVE FIELDS

(71) Applicant: MicroCube, LLC, Fremont, CA (US)

(72) Inventors: Ketan Shroff, Pleasanton, CA (US);
Dinesh I. Mody, San Jose, CA (US);
Michael Dobrowski, San Francisco, CA (US)

(73) Assignee: MicroCube, LLC, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/051,974

(22) Filed: Feb. 12, 2025

(65) Prior Publication Data

US 2025/0186116 A1     Jun. 12, 2025

Related U.S. Application Data

(63) Continuation of application No. 16/912,607, filed on Jun. 25, 2020, now Pat. No. 12,239,367.

(60) Provisional application No. 62/866,609, filed on Jun. 25, 2019.

(51) Int. Cl.
| | |
|---|---|
| *A61B 18/18* | (2006.01) |
| *A61B 18/00* | (2006.01) |
| *H01Q 3/01* | (2006.01) |
| *H01Q 21/06* | (2006.01) |

(52) U.S. Cl.
CPC ............ *A61B 18/1815* (2013.01); *H01Q 3/01* (2013.01); *H01Q 21/061* (2013.01); *A61B 2018/00577* (2013.01); *A61B 2018/1823* (2013.01); *A61B 2018/1861* (2013.01); *A61B 2018/1884* (2013.01)

(58) Field of Classification Search
CPC ...... A61B 18/1815; A61B 2018/00351; A61B 2018/00488; A61B 2018/00494; A61B 2018/00529; A61B 2018/00559; A61B 2018/00571; A61B 2018/00577; A61B 2018/1823; A61B 2018/1861; A61B 2018/1884; H01Q 21/061; H01Q 3/01
See application file for complete search history.

(56) References Cited

U.S. PATENT DOCUMENTS

| | | | |
|---|---|---|---|
| 4,583,556 A | 4/1986 | Hines et al. |
| 4,658,836 A | 4/1987 | Turner |
| 4,700,716 A | 10/1987 | Kasevich et al. |
| 5,007,437 A | 4/1991 | Sterzer |
| 5,057,106 A | 10/1991 | Kasevich et al. |
| 5,129,396 A | 7/1992 | Rosen et al. |
| 5,277,201 A | 1/1994 | Stern |
| 5,449,380 A | 9/1995 | Chin |
| 5,603,697 A | 2/1997 | Grundy et al. |
| 5,741,249 A | 4/1998 | Moss et al. |
| 5,769,880 A | 6/1998 | Truckai et al. |

(Continued)

FOREIGN PATENT DOCUMENTS

| | | |
|---|---|---|
| EP | 1145686 | 10/2001 |
| EP | 1298542 | 4/2003 |

(Continued)

*Primary Examiner* — Tigist S Demie
(74) *Attorney, Agent, or Firm* — Levine Bagade Han LLP

(57) ABSTRACT

Microwave antennas and devices incorporating such antennas usable for performing procedures on or within a patient's body using a shaped microwave field.

20 Claims, 19 Drawing Sheets

(56) References Cited

U.S. PATENT DOCUMENTS

| | | | |
|---|---|---|---|
| 5,788,692 A | 8/1998 | Campbell et al. |
| 5,861,021 A | 1/1999 | Thome et al. |
| 5,902,251 A | 5/1999 | Vanhooydonk |
| 5,928,145 A | 7/1999 | Ocali et al. |
| 5,957,969 A | 9/1999 | Warner et al. |
| 6,210,367 B1 | 4/2001 | Carr |
| 6,287,302 B1 | 9/2001 | Berube |
| 6,306,132 B1 | 10/2001 | Moorman et al. |
| 6,381,483 B1 | 4/2002 | Hareyama et al. |
| 6,471,696 B1 | 10/2002 | Berube et al. |
| 6,503,247 B2 | 1/2003 | Swartz et al. |
| 6,635,055 B1 | 10/2003 | Cronin |
| 6,663,625 B1 | 12/2003 | Ormsby et al. |
| 6,813,520 B2 | 11/2004 | Truckai et al. |
| 6,817,999 B2 | 11/2004 | Berube et al. |
| 6,929,642 B2 | 8/2005 | Xiao et al. |
| 7,197,363 B2 | 3/2007 | Prakash et al. |
| 7,226,446 B1 | 6/2007 | Mody et al. |
| 7,864,160 B2 | 1/2011 | Geaghan et al. |
| 8,808,281 B2 | 8/2014 | Emmons et al. |
| 8,968,287 B2 | 3/2015 | Shroff et al. |
| 9,462,642 B2 | 10/2016 | Chu et al. |
| 9,615,882 B2 | 4/2017 | Shroff et al. |
| 9,980,774 B2 | 5/2018 | Chu et al. |
| 9,993,293 B2 | 6/2018 | Chu et al. |
| 10,299,859 B2 | 5/2019 | Chu et al. |
| 10,329,484 B2 | 6/2019 | Kovalenko et al. |
| 10,470,819 B2 | 11/2019 | Chu et al. |
| 10,859,720 B2 | 12/2020 | Prokop et al. |
| 10,869,720 B2 | 12/2020 | Chu et al. |
| 11,147,619 B2 | 10/2021 | Chu et al. |
| 11,219,484 B2 | 1/2022 | Chu et al. |
| 11,291,503 B2 | 4/2022 | Emmons et al. |
| 11,684,418 B2 | 6/2023 | Chu et al. |
| 12,239,367 B2 | 3/2025 | Mody et al. |
| 2003/0057413 A1 | 3/2003 | Kim et al. |
| 2003/0109868 A1 | 6/2003 | Chin et al. |
| 2003/0163128 A1 | 8/2003 | Patil et al. |
| 2003/0195499 A1 | 10/2003 | Prakash et al. |
| 2004/0002703 A1 | 1/2004 | Xiao et al. |
| 2005/0015081 A1 | 1/2005 | Turovskiy et al. |
| 2005/0240173 A1 | 10/2005 | Palti |
| 2006/0200119 A1 | 9/2006 | Vaska et al. |
| 2006/0293652 A1 | 12/2006 | Van Der Weide |
| 2007/0066972 A1 | 3/2007 | Ormsby et al. |
| 2007/0139294 A1 | 6/2007 | Dunn et al. |
| 2007/0179552 A1 | 8/2007 | Dennis et al. |
| 2007/0203480 A1 | 8/2007 | Mody et al. |
| 2007/0213583 A1 | 9/2007 | Kim et al. |
| 2008/0082093 A1 | 4/2008 | Prakash et al. |
| 2008/0167664 A1 | 7/2008 | Payne et al. |
| 2009/0146439 A1 | 6/2009 | Watts et al. |
| 2010/0121319 A1 | 5/2010 | Chu et al. |
| 2010/0125269 A1 | 5/2010 | Emmons et al. |
| 2010/0137857 A1 | 6/2010 | Shroff et al. |
| 2010/0137860 A1 | 6/2010 | Demarais et al. |
| 2011/0004205 A1 | 1/2011 | Chu et al. |
| 2011/0040300 A1 | 2/2011 | Brannan |
| 2011/0257641 A1 | 10/2011 | Hastings et al. |
| 2012/0116486 A1 | 5/2012 | Naga et al. |
| 2013/0256302 A1 | 10/2013 | Chu et al. |
| 2014/0290830 A1 | 10/2014 | Brannan |
| 2014/0358140 A1 | 12/2014 | Emmons et al. |
| 2015/0313670 A1 | 11/2015 | Shroff et al. |
| 2016/0015259 A1 | 1/2016 | Mody et al. |
| 2017/0273730 A1 | 9/2017 | Walke et al. |
| 2018/0036080 A1 | 2/2018 | Dickhans et al. |
| 2018/0303547 A1 | 10/2018 | Chu et al. |
| 2018/0318005 A1 | 11/2018 | Chu et al. |
| 2018/0325592 A1 | 11/2018 | Emmons et al. |
| 2018/0344397 A1 | 12/2018 | Chu et al. |
| 2019/0380776 A1 | 12/2019 | Chu et al. |
| 2020/0121388 A1 | 4/2020 | Chu et al. |
| 2020/0405389 A1 | 12/2020 | Shroff et al. |
| 2021/0205014 A1 | 7/2021 | Chu et al. |
| 2022/0000553 A1 | 1/2022 | Chu et al. |
| 2022/0249163 A1 | 8/2022 | Emmons et al. |
| 2024/0000505 A1 | 1/2024 | Chu et al. |
| 2024/0415575 A1 | 12/2024 | Emmons et al. |
| 2025/0114142 A1 | 4/2025 | Mody et al. |

FOREIGN PATENT DOCUMENTS

| | | |
|---|---|---|
| EP | 1511315 | 3/2005 |
| JP | 2001-231790 | 8/2001 |
| JP | 2002-017745 | 1/2002 |
| JP | 2005-512668 | 5/2005 |
| JP | 2005-312807 | 11/2005 |
| JP | 2005-534352 | 11/2005 |
| JP | 2007-535369 | 12/2007 |
| KR | 10-2018-0095832 | 8/2018 |
| WO | WO 1997/006739 | 2/1997 |
| WO | WO 2002/011445 | 2/2002 |
| WO | WO 2003/053259 | 7/2003 |
| WO | WO 2003/088858 | 10/2003 |
| WO | WO 2006/004585 | 1/2006 |
| WO | WO 2008/071914 | 6/2008 |
| WO | WO 2009/146439 | 12/2009 |
| WO | WO 2010/048334 | 4/2010 |
| WO | WO 2010/048335 | 4/2010 |
| WO | WO 2010/053700 | 5/2010 |
| WO | WO 2012/003232 | 1/2012 |
| WO | WO 2013/149245 | 10/2013 |
| WO | WO 2020/264209 | 12/2020 |

Arrow Volume Electric field (V/m)

Arrow Volume Electric field (V/m)

Time-125s isosurface: Temperature (deg C)

Time-175s isosurface: Temperature (deg C)

Time-125s isosurface: Temperature (deg C)

Time-175s isosurface: Temperature (deg C)

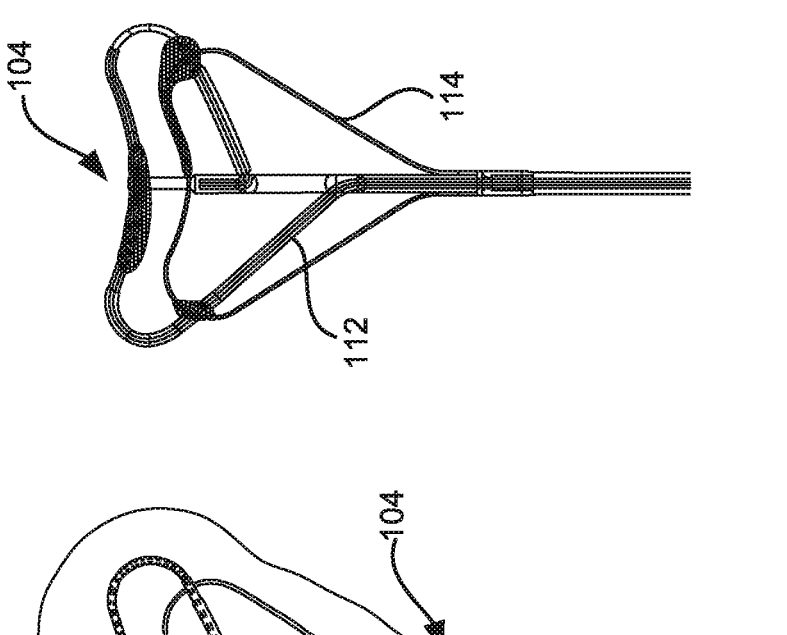
FIG. 7C
FIG. 7B
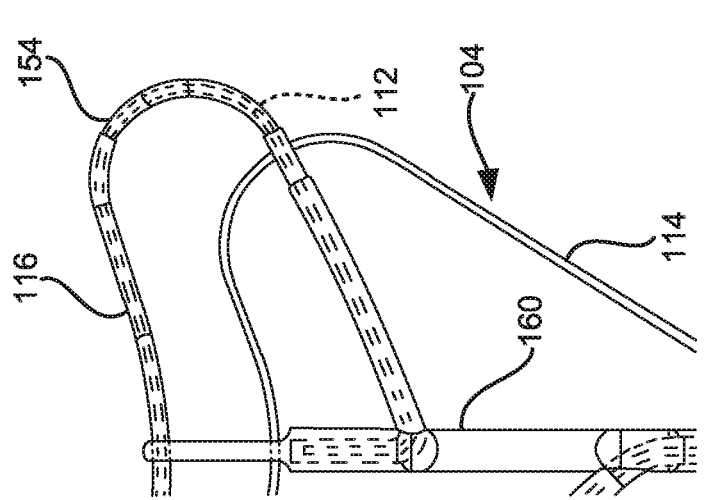
FIG. 7A

METHODS AND DEVICES FOR GENERATING AND DELIVERING SHAPED MICROWAVE FIELDS

CROSS-REFERENCE TO RELATED APPLICATION DATA

This application is a continuation of U.S. patent application Ser. No. 16/912,607, filed Jun. 25, 2020, which claims benefit to U.S. Provisional Application No. 62/866,609, filed Jun. 25, 2019, which is incorporated by reference in its entirety.

BACKGROUND

Menorrhagia is one of the most common gynecological conditions in pre-menopausal women and is characterized by excessive menstrual blood loss. Objectively, Menorrhagia can be defined as blood loss of more than 80 ml per menstrual cycle. The condition severely affects the quality of life of the affected women since it can interfere with physical activity, work and sexual activity. In some cases, it leads to iron deficiency anemia.

The usual first line of treatment is drugs such as oral contraceptive pills and synthetic Progesterone supplements. However, drugs are not effective in a significant percentage of patients. In patients with refractory disease, the classical treatment is hysterectomy, which is an invasive surgery involving the removal of the uterus. In many cases, the surgery requires 2-4 days of hospitalization and has a 3 to 6 week recovery period. Further, it carries risks due to the use of general anesthesia and those risks associated with any invasive surgery on a major organ in the body.

Endometrial ablation is an alternative to a hysterectomy. There are several endometrial ablation techniques that ablate only the endometrium in a minimally invasive manner. Such techniques can include radiofrequency heating, circulating hot saline in the uterine cavity, microwave heating, cryoablation, laser ablation, etc. Endometrial ablation in general has been established as an effective therapy for the treatment of Menorrhagia. However, current endometrial ablation devices include shafts that are thick and rigid. Because of this, an amount of cervical dilation required to insert the device into the uterine cavity can cause extreme patient discomfort. In some cases, the pain associated with cervical dilation requires administering anesthesia to the patient, usually in the form of conscious sedation or general ANESTHESIA. Further, the active end of many devices has a fixed shape that often does not conform to irregularly shaped uterine cavities. Some current devices are unable to create an ablation zone that matches to the complex, three-dimensional shape of the endometrial layer. Thus, even though there are a variety of endometrial ablation products, there is still room for improvement to provide a small-size, flexible, easy to use device.

The present disclosure includes microwave devices and methods of use that generate uniquely shaped microwave fields to improve outcomes in endometrial ablation as well as other medical conditions, such as cardiac electrophysiological disorders, cancer treatment, etc., where uniform application of energy is beneficial.

SUMMARY

The microwave antennas described herein can avoid common disadvantages to previous microwave devices such as device shaft heating and non-uniform lesion profile along the length of the antenna.

The present disclosure includes medical devices for treating tissue by applying a microwave energy from a transmission line coupled to a power supply to produce a shaped microwave field. For example, one such device can include an antenna comprising a radiating element, a shaping element and a dielectric piece/shaft; the shaping element being electrically grounded using to the power supply; the dielectric piece extending along an axis of the antenna; and the radiating element having a first end and a second end, and a middle portion therebetween which collectively form a working profile, the radiating element being flexible to have a delivery profile when constrained and to assume the working profile when unconstrained, wherein the first end and second end are offset along the axis of the antenna and extend from the axis in opposite directions; wherein application of microwave energy to the antenna generates a microwave field having a volumetric shape.

Variations of any antenna described herein can include a planar or non-planar working profile. For example, the radiating element and/or shaping element can lie within a single geometric plane. Alternately, the radiating element and/or shaping element can be curved such that the rounded ends of the radiating element and/or shaping element are not in the same geometric plane. In one example, the rounded ends of the radiating element and/or shaping element can be out-of-plane with the middle portion of the antenna.

A variation of the device can include wherein the first end and second end of the radiating element are linear. Another variation of the device can include a first non-linear region between the first end and the middle portion and a second-non-linear region between the second end and the middle portion. In another variation, the middle portion is non-linear. The middle portion can extend transversely relative to the axis.

Variation of the devices described herein can include a portion of the shaping element being located adjacent to the radiating element to produce a highest concentration of the microwave field towards a distal portion of the antenna.

In additional variations of the device, the first end of the radiating portion extends from a first location on the dielectric piece and/or the second end of the radiating portion extends from a second location on the dielectric piece.

Variations of the device can include a dielectric piece having a stepped outer diameter. Additionally, or in combination variations of the device can include an outer dimension of the dielectric covering to vary on the radiating element. In additional variations, the dielectric covering comprises a plurality of different dielectric materials.

Variations of an antenna can include a bend angle by which the second portion is bent relative to the radiating element immediately proximal to the second portion is greater than 90 degrees.

In an additional variation, a distal tip of the radiating element points in the distal direction. Another configuration of the antenna includes the first portion and the second portion being parallel to each other.

Another variation of a medical device for treating tissue includes a transmission line coupled to the power supply; an antenna comprising a radiating element, a shaping element and a dielectric piece; the shaping element being electrically grounded using to the power supply; the dielectric piece extending along an axis of the antenna; and the radiating element having a first end and a second end, and a middle portion therebetween which collectively form a working profile, the radiating element being flexible to have a delivery profile when constrained and to assume the working profile when unconstrained, wherein the first end and second end are offset along the axis of the antenna and extend from the axis in opposite directions; wherein application of microwave energy to the antenna generates a microwave field having a volumetric shape.

A method of delivering energy to tissue within a cavity, the method comprising: A method of delivering energy to tissue within a cavity, the method comprising: inserting a microwave antenna into the cavity, the microwave antenna comprising a shaping element and a radiating element having a working configuration when unconstrained, wherein a distal portion of the radiating element extends transversely to an axis of the microwave antenna; positioning the distal portion of the radiating element against a surface of the cavity, wherein the distal portion of the radiating element is configured to conform to a surface of the cavity before distorting the cavity, and where a remainder of radiating element remains in the working configuration; and applying energy to microwave antenna through a transmission line that is coupled to an energy source, where during the application of energy, the shaping element shapes the microwave field of the radiating element to generate a volumetric microwave field wherein a highest concentration of microwave energy is at a distal region of the antenna.

In another variation, the method can include the radiating element and the shaping element configured to produce the microwave field that is wider at a distal area and narrower at a proximal area.

BRIEF DESCRIPTION OF THE FIGURES

FIG. 7A shows the design details of an alternate variation of an antenna.

FIGS. 7B, 7C, and 7D show the electromagnetic field shape, location of hot spots, and the matching of the antenna of FIG. 7A.

FIG. 7E shows the design details of another variation of an antenna.

FIGS. 7F, 7G, and 7H show the electromagnetic field shape, location of hot spots, and the matching of the antenna of FIG. 7E.

FIG. 7I shows the design details of a variation of an antenna.

FIGS. 7J, 7K, and 7L show the electromagnetic field shape, location of hot spots, and the matching of the antenna of FIG. 7I.

FIG. 7M shows the design details of another variation of an antenna.

FIGS. 7N, 7O, and 7P show the electromagnetic field shape, location of hot spots, and the matching of the antenna of FIG. 7M.

FIG. 7Q shows the design details of another variation of an antenna.

FIGS. 7R, 7S, and 7T show the electromagnetic field shape, location of hot spots, and the matching of the antenna of FIG. 7Q.

DETAILED DESCRIPTION

Figures 1A, 1B:
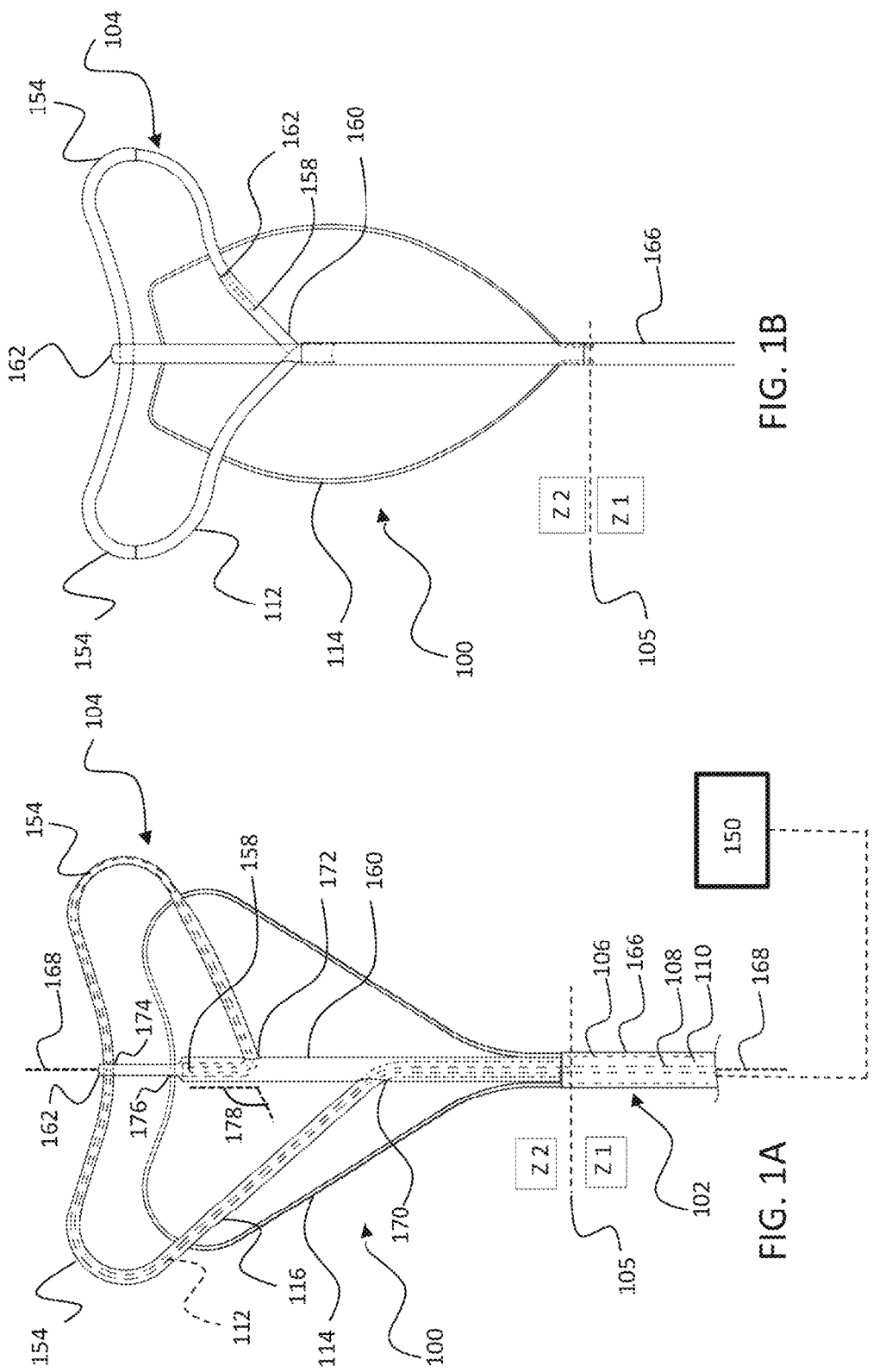
FIG. 1A shows a front view of a planar antenna optimized for endometrial ablation.
FIG. 1B shows an example of an older antenna for comparing the improvements of the improved antenna disclosed herein.

This specification discloses multiple antenna designs, systems, and associated methods for producing improved microwave fields. While these devices and associated methods are discussed primarily in terms of endometrial ablation, the methods and devices disclosed herein are applicable for use in other bodily structures, as well as other areas where microwave fields are required. Methods and devices disclosed herein can be used for ablating tissue in, or adjacent to, the brain, prostate gland, portions of the urinary tract, gall bladder, uterus and other portions of the female reproductive tract, regions of the vasculature, intestines and other portions of the lower alimentary tract, stomach and other portions of the upper alimentary tract, liver and other digestive organs, lungs, skin, mucus membranes, kidneys, reproductive organs, joints, or other organs or soft tissues of the body. The devices and methods disclosed herein may be used for the treatment of knee disorders, anterior cruciate ligament instability, vertebral disk injuries and chronic low back pain. The devices and methods disclosed herein may be used several arthroscopic applications such as shrinking the tissues of the ligamentous joint capsule to increase the tension on these ligaments for stabilizing the shoulder joint.

Several devices and methods disclosed herein may be used to treat tissue by microwave thermal ablation. Even though a significant portion of the disclosure is about microwave devices and methods for ablation of tissue to kill or otherwise damage tissue, microwave energy may be applied to tissue to achieve a variety of clinically useful effects other than ablation. Examples of such effects include, but are not limited to: 1. causing heat-induced modification of tissue (e.g. heat shrinkage or other alteration in the properties of collagen), 2. causing heat-induced modification of an artificially introduced material (e.g. heat induced polymerization of an injected monomer), 3. warming tissue to change the metabolic activity of tissue (e.g. warming tissue to increase metabolism), 4. causing fat liquefaction e.g. to ease fat extraction during microwave-assisted lipoplasty, 5. causing controlled tissue death to debulk tissue for treating conditions such as obstructive sleep apnea, 6. delivering energy to tissue to change the electrophysiological characteristics of that tissue, and 7. increasing the efficacy of a therapy (e.g. chemotherapy) in a local region of tissue. Microwave emitting device embodiments herein may be used for methods that do not involve ablation of tissue.

Antennas disclosed herein can ablate or otherwise treat planar or non-planar tissue regions. Antennas disclosed herein may comprise single or multiple splines, curves or loops. Such structures may be oriented in a generally planar arrangement. Antennas disclosed herein may be used for ablating a surface such as the surface of organs such as liver, stomach, esophagus, a heart chamber, etc.

The features disclosed herein are related to US patent application publication no. 2011/0004205 and US patent publication no. 2018/0318005. The antennas can be used for methods including, but not limited to the methods disclosed in US patent publication no. 2011/0004205 and US patent publication no. 2018/0318005, U.S. Pat. No. 9,462,642, US patent publication no. 2016/0015259, US patent publication no. 2017/0273730. This application is also related to PCT/US2020/039683 filed on Jun. 25, 2020. The entire disclosures of each of the documents listed in this disclosure are incorporated by reference.

Figure 3B:
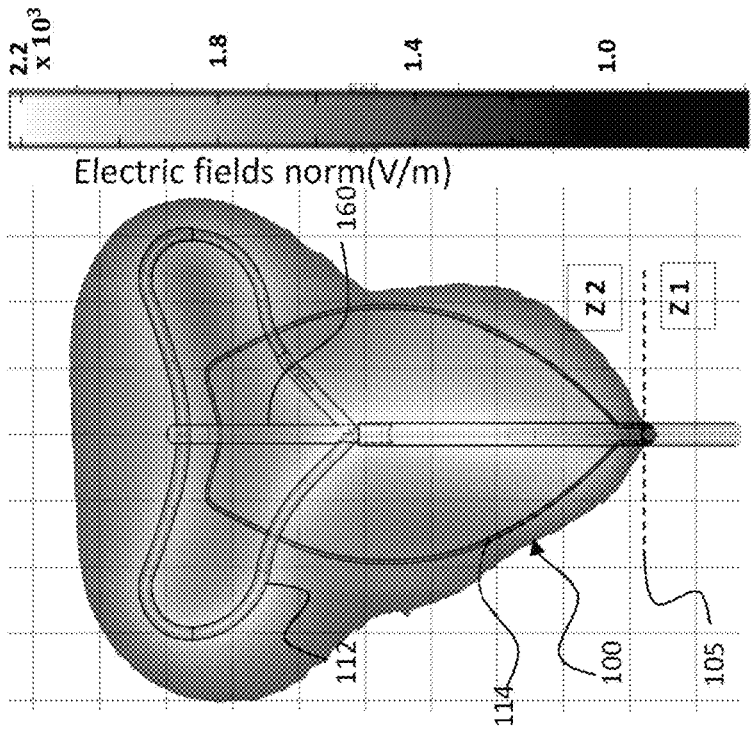

Several figures herein have gridlines for showing the dimensions of the embodiment(s) shown in that figure. The dimensions of a square box in FIGS. 3A-3B, 4A-4C, 5A-5B, 7A-7C, 7E-7G, 7I-7K, 7M-7O, 7Q-7S, and 7U-7W is 5 mm×5 mm. The dimensions of a rectangular box in FIGS. 5C-5D is 5 mm×2 mm. Although the devices might be described in terms of particular dimensions in the figures, unless explicitly stated, the claims are not limited by any specific dimension.

FIG. 1A shows a front view of an antenna 104 of a microwave ablation device, where the antenna includes a radiating element 112 typically encased in a dielectric or polymeric material 116 and coupled to a dielectric piece 160. The antenna can optionally include one or more shaping elements 114, as described herein, the presence of a shaping element 114 adjacent to the radiating element 112 shapes the resulting microwave field. In the present example, the antenna 104 is optimized for endometrial ablation. FIG. 1A shows that the antenna 104 can be part of a microwave ablation system 100 having a transmission line (such as a coaxial cable 102) that is coupled to a power supply 150. In some variations, the antenna 104 can be coupled onto a transmission line. In other variations, the transmission line terminates with the antenna 104 at the distal end of the transmission line such that the antenna 104 is not intended for decoupling from the transmission line 102. In any case, the radiating element 112 is electrically coupled to an inner conductor 108 of the transmission line 102 while the shaping element 114 may be electrically grounded. Usually, the shaping element 114 is electrically connected to outer conductor 106 of the transmission line 102. However, the shaping element 114 can be electrically grounded using a separate electrical connection. In additional variations, the shaping member 114 is grounded to an electrical ground that is separate from the power supply 150.

System 100 can be divided into a first zone Z1 that is proximal and a second zone Z2 by an imaginary transition line 105. Transition line 105 is defined by the distal end of transmission line (such as a coaxial cable 102) and is substantially perpendicular to the axis of the transmission line at the distal end of coaxial cable 102. In the embodiment shown in FIG. 1A, the distal region of coaxial cable 102 lies entirely within first zone Z1 and antenna 104 lies entirely within second zone Z2. In one embodiment, a microwave signal is fed to antenna 104 through coaxial cable 102. Antenna 104 generates a microwave field. The near field of the microwave field generated by antenna 104 may be used for tissue ablation.

In FIG. 1A, antenna 104 comprises a radiating element 112 in the form of an outer loop and a shaping element 114 in the form of a metallic center loop. Radiating element 112 and shaping element 114 may physically touch each other when deployed in the anatomy. In one embodiment, radiating element 112 is a continuation of the inner conductor 108 of coaxial cable 102. Shaping element 114 shapes or redistributes the microwave field radiated by radiating element 112. It should be noted that there is no direct electrical contact between radiating element 112 and shaping element 114. When microwave energy is delivered through coaxial cable 102 to antenna 104, a first microwave field is emitted by radiating element 112. The first microwave field interacts with shaping element 114. This interaction induces a leakage current on shaping element 114. The leakage current in turn creates a second microwave field. The first microwave field and the second microwave field together combine to produce a unique shaped microwave field of antenna 104 that is clinically more useful that the unshaped microwave field generated by an antenna 104 comprising only radiating element 112. Thus, the original microwave field is redistributed by the design of shaping element 114. Shaping element 114 alone is not capable of functioning as an antenna; rather shaping element 114 shapes or redistributes the electromagnetic or microwave field emitted by radiating element 112 to produce a shaped microwave field that is clinically more useful. Further, the combination of radiating element 112 and shaping element 114 improves the power deposition of antenna 104.

In one embodiment, radiating element 112 has no sharp corners. Sharp corners in radiating element 112 may cause the field to concentrate in the vicinity of the sharp corners. In one embodiment, the minimal radius of curvature of a corner in radiating element 112 is at least 1.0 mm. In the embodiment in FIG. 1A, the radius of curvature of the two corner regions 154 in radiating element 112 is at least 1.0 mm.

In one embodiment, antenna 104 has a shape that substantially approximates the shape of the body organ to be ablated. For example, antenna in FIG. 1A has a roughly triangular shape that approximates the shape of the uterine cavity and is especially suited for endometrial ablation. The proximal portion of the antenna 104 is directed towards the cervix and corner regions 154 of radiating element 112 are directed towards the cornua when positioned within the uterine cavity. However, as mentioned before, microwave thermal ablation does not necessarily require perfect contact with the entire target tissue. Thus antenna 104 is able to ablate all or substantially all of the endometrium without antenna 104 physically touching the entire endometrium. The entire endometrium can be ablated in a single ablation by antenna 104 having a single microwave antenna. Thus, repositioning of antenna 104 after an ablation is not needed. This greatly reduces the amount of physician skill needed for the procedure. Further, multiple antennas 104 are not needed in ablation system 100. A single antenna 104 positioned at a single location is able to ablate a therapeutically sufficient amount of the endometrium. This simplifies the design of ablation system 100. Antenna 104 may be repositioned as needed to treat larger cavities.

Further, antenna 104 in the working configuration is generally flat and flexible. The plane of radiating element 112 is substantially parallel to the plane of shaping element 114. Thus, the uterine walls experience only slight forces from antenna 104. This in turn reduces or eliminates the distension of the uterine wall thereby reducing the discomfort to the patient. This in turn further reduces the anesthesia requirements. Flexible antenna 104 may easily be introduced in a collapsed configuration through a small lumen (e.g. a lumen of an introducing device) thereby eliminating or minimizing any cervical dilation. This dramatically reduces the discomfort to the patient consequently significantly reducing the requirement of anesthesia.

Further, flat and flexible antenna 104 in FIG. 1A in its deployed configuration has an atraumatic distal end in which the distal region of antenna 104 is wider than the proximal portion of antenna 104. This reduces the risk of perforation of the uterus. The flexible nature of antenna enables antenna 104 to take the natural shape of the introduction passage instead of distorting the passage. For example, when antenna 104 is introduced trans-cervically into the uterus, antenna 104 may itself get distorted while passing through the introduction passage comprising the vagina, cervical canal and uterine cavity instead of distorting one or more of the vagina, cervical canal and uterine cavity.

In one embodiment of a deployed configuration of antenna 104 as shown in FIG. 1A, the length of radiating element 112 measured along the radiating element 112 from the distal end of coaxial cable 102 until the distal end 158 of radiating element 112 is about three quarters of the effective wavelength at the 915 MHz ISM band. In other embodiments, the length of outer loop 112 measured along the outer loop 112 from the distal end of coaxial cable 102 or other transmission line until the distal end of outer loop 112 is an odd multiple of one quarter of the effective wavelength at one of: 433 MHz ISM band, 915 MHz ISM band, 2.45 GHz ISM band and 5.8 GHz ISM band. The effective wavelength is dependent on the medium surrounding the antenna and the design of an antenna dielectric on the radiating element 112. The design of the antenna dielectric includes features such as the type of dielectric(s) and thickness of the dielectric layer(s). In one embodiment, the exact length of the radiating element 112 is determined after tuning the length of radiating element 112 to get good impedance matching. The length of the radiating element 112 in one embodiment is 100+/−50 mm. In one embodiment, the width of deployed radiating element 112 is 40+/−25 mm and the longitudinal length of deployed radiating element 112 measured along antenna axis 168 from plane 105 till the distal most region of radiating element 112 is 35+/−15 mm. In the embodiment shown in FIG. 1A, an antenna dielectric 116 in the form of a straight (linear) dielectric piece 160 comprising a distal end 162 is located roughly at the center of antenna 104. Dielectric piece 160 provides sites for mechanical attachment or coupling of various regions of antenna 104 and helps antenna 104 to be deployed from and retracted into an introducing sheath. Dielectric piece 160 has sites for mechanical attachment or coupling of distal regions of radiating element 112 and shaping element 114 as shown.

In one variation of the antenna 104, a dielectric piece 160 comprises three openings. A first proximal opening 170 accommodate passage of a first end of the radiating element 112 and surrounding dielectric covering 116. A middle opening 172 that receives a second end 158 of the radiating element 112 and surrounding dielectric covering 116. An opening 174 to accommodate passage of a region of the radiating element 112 and an opening 176 to accommodate passage of a region of the shaping element 114. As noted herein, in some devices it is desirable to minimize a delivery profile of the device to minimize the size required of any introducer sheath or member through which the device passes to enter a tissue cavity. Passage of the radiating element 112 (and optionally the dielectric covering 116) into the dielectric piece 160 allows for a delivery profile to minimized since there are no external joints, connection point, and/or fasteners that would otherwise increase a diameter of the dielectric piece 160. In the variation of FIG. 1A, the first end and second end of the radiating element are offset along the axis 168 of the antenna 104 and extend from the axis in opposite directions. The ends of the radiating element can originate and terminate from the dielectric piece 160 as shown.

Any of the antenna variations disclosed herein can have a working profile (e.g., the profile when the antenna is unconstrained and energy is applied to tissue), where the working profile can be planar. However, the working profile can also be non-planar if the two sides of the antenna 104 are not completely within a single plane. As seen in FIG. 1A, a region of radiating element 112 extends away from first proximal opening 170. Also, as seen in FIG. 1A, a region of radiating element 112 extends away from second proximal opening 172. One or more portions of dielectric piece 160 proximal to first proximal opening 170 and/or second proximal opening 172 may have one or more bumps or raised regions. These regions help to guide a deployment device (e.g. a deployment sheath) when the deployment device is slid over antenna 104. The guiding of deployment device in turn helps to antenna 104 to fold, which in turn helps with the introduction of antenna 104 into the deployment device. Dielectric piece 160 also comprises a second distal opening 176 through which a region of shaping element 114 passes. Shaping element 114 may be mechanically attached or coupled to a region of dielectric piece 160 near second distal opening 176. Dielectric piece 160 may be attached to radiating element 112 and shaping element 114 by one or more methods including, but not limited to: glues or adhesives, mechanical fastening structures, heat shrinkable elements, friction fit, etc. Distal end 158 of radiating element 112 is inserted into dielectric piece 160 through opening 172 as shown. Distal end 158 of radiating element 112 may be mechanically attached to dielectric piece 160. The mechanical attachment may be made by one or more of: glues or adhesives, mechanical fastening structures, heat shrinkable elements, etc. As seen in FIG. 1A, a portion of radiating element 112 near opening 172 acts like a hinge by taking an acute bend during the use of system 100 (e.g. while introducing antenna 104 into a lumen). In contrast, in the embodiment of FIG. 1B, a portion of dielectric piece 160 acts as a hinge. As seen in FIG. 1A, bend angle 178 is greater than 90 degrees. Bend angle 178 is defined as the angle by which radiating element 112 bends at the distal region of radiating element 112.

In one embodiment, a proximal portion of radiating element 112 is designed to be stiffer and have greater mechanical strength than a distal portion. This may be achieved by leaving original dielectric material 110 of coaxial cable 102 on the proximal portion of radiating element 112. In an alternate embodiment, this is achieved by coating a proximal portion of radiating element 112 by a layer of antenna dielectric 116.

The cross-sectional shape of radiating element 112 may not be uniform along the entire length of radiating element 112. In one such embodiment, the proximal portion of radiating element 112 is a continuation of inner conductor 108 of coaxial cable 102. This portion has a substantially circular cross section. A middle portion of radiating element 112 has a substantially flattened or oval or rectangular cross section. At least a part of the middle portion may be oriented generally perpendicular to the distal region of coaxial cable 102 in the deployed configuration as shown in FIG. 1A. In FIG. 1A, the part of radiating element 112 near tip 162 is oriented perpendicular to the antenna axis. A portion of radiating element 112 has a sufficient mechanical flexibility to bend in a plane after deployment in the anatomy. This in turn ensures that the distal most region of ablation system 100 is atraumatic and flexible enough to conform to the target tissue anatomy. This helps in the proper deployment of radiating element 112 in the uterus. In one embodiment, a middle portion of radiating element 112 is a continuation of inner conductor of coaxial cable 102 and is flattened. In one embodiment, the distal most portion of radiating element 112 is a continuation of inner conductor of coaxial cable 102 and is non-flattened such that it has a circular cross section. In one embodiment, radiating element 112 is made of a length of a Nitinol or stainless-steel wire. A distal portion of the wire may be deformed (e.g. by flattening) or may comprise a portion where one or more materials have been removed (e.g. by grinding, laser machining, EDM, etc.). Radiating element 112 may be plated, clad or otherwise covered with a layer of highly conductive materials such as gold or silver. Such a wire may be used to replace the inner conductor 108 of coaxial cable 102. This assembly may then be used to construct microwave system 100. In another embodiment, radiating element 112 is made of a length of a Nitinol or stainless-steel wire clad with a layer of highly conductive materials such as gold or silver. A distal portion of the wire is deformed (e.g. by flattening). This wire is used to replace the inner conductor 108 of coaxial cable 102. This assembly is then used to construct microwave system 100.

The embodiment of FIG. 1A also shows the distal end of the radiating element 112 is enclosed within dielectric piece 160. In this embodiment, the distal end of radiating element 112 is linear and points in the distal direction and is oriented parallel to the antenna axis and dielectric piece 160. In an alternate embodiment, the distal end of radiating element 112 is mechanically attached to a region of dielectric piece 160 without being entirely enclosed within dielectric piece 160. In one such embodiment, the distal end of radiating element 112 is mechanically attached to a region of dielectric piece 160 and is located outside dielectric piece 160. In alternate embodiments, the distal end of radiating element 112 is located near dielectric piece 160 without being oriented parallel to the antenna axis and dielectric piece 160.

In the embodiment shown in FIG. 1A, dielectric piece 160 is linear with a tapered portion (with a stepped outer diameter) proximal to second distal opening 176. In alternate embodiments, dielectric piece 160 has a non-linear shape. Dielectric piece 160 may be constructed from a material selected from the group including, but not limited to: PEEK, PEBAX, ABS and other relatively stiff polymer materials. Dielectric piece 160 may contain one or more metallic or conductive regions. The one or more metallic or conductive regions may be used to alter the thermal profile and/or the matching of antenna 104. An additional function of the dielectric piece 160 is to provide the user with force feedback about the proper position of the device inside a uterus. In one embodiment of a clinical procedure, antenna 104 is inserted in a folded/collapsed, undeployed/constrained configuration through an introducing sheath into the uterine cavity. Thereafter, antenna 104 is pushed distally relative to the introducing sheath to deploy antenna 104 out of the distal end of the introducing sheath. This causes antenna 104 to attain the deployed/unconstrained configuration as shown in FIG. 1A. This is a working profile wherein antenna 104 may be used for performing one or more medical procedures. Thereafter, antenna 104 is pushed distally such that the distal most region of antenna 104

(distal end region 162 of dielectric piece 160) pushes against the fundus. The sufficiently stiff dielectric piece 160 causes the user to feel a resistance as soon as the distal most region of antenna 104 pushes against the fundus. This in turn provides the user with a force feedback about the position of antenna 104 against the fundus.

In one embodiment, dielectric piece 160 comprises a lumen that communicates with first proximal opening 170 and second proximal opening 172. Portion of radiating element 112 are located within this lumen. One or more portions of the lumen (e.g. a portion between first proximal opening 170 and second proximal opening 172) may be filled with glue or other materials. In an alternate embodiment, one or more hollow portions or cavities in dielectric piece 160 are used to enclose and/or attach portions of radiating element 112. Dielectric piece 160 may be made of a single piece of material or could be made of multiple elements that are attached to each other. Dielectric piece 160 may be made by methods including, but not limited to: molding, gluing, extruding, machining, 3D printing, etc.

One or more outer surfaces of radiating element 112 may be covered with one or more layers of antenna dielectrics 116. One or more outer surfaces of shaping element 114 may be covered with one or more layers of antenna dielectrics. The thickness and type of antenna dielectric material along the length of radiating element 112 may be engineered to optimize the microwave field shape. In the embodiment shown in FIG. 1A, every portion of radiating element 112 is covered with some antenna dielectric material such that no metallic surface of radiating element 112 is exposed to tissue. Thus, in the embodiment of FIG. 1A, radiating element 112 is able to transmit a microwave field into tissue, but unable to conduct electricity to tissue. Thus, in the embodiment of FIG. 1A, there is no electrical conduction and no conductive path between radiating element 112 and shaping element 114 even though radiating element 112 and shaping element 114 may physically touch each other when deployed in the anatomy. Examples of dielectric materials that can be used as antenna dielectrics 116 in one or more embodiments disclosed herein include, but are not limited to EPTFE, PTFE, FEP, PFA and other fluoropolymers, Silicone, Air, PEEK, polyimides, cyanoacrylates, polyolefins, epoxy, natural or artificial rubbers and combinations thereof. The antenna dielectric 116 on the proximal portion of radiating element 112 may be a continuation of a dielectric of coaxial cable 102. There may be an additional layer of a stiffer antenna dielectric 116 over this layer of antenna dielectric 116 on the proximal portion of radiating element 112.

In the embodiment of FIG. 1A, the dielectric on radiating element 112 is a blend of polyolefins. In another embodiment, the dielectric on the middle portion of radiating element 112 is a dielectric layer with or without impregnated air or dielectric tube enclosing a layer of air or EPTFE. In another embodiment, the dielectric on the distal most portion of radiating element 112 is a dielectric layer with or without impregnated air or a dielectric tube enclosing a layer of air or EPTFE. The thickness of an antenna dielectric on any portion of radiating element 112 may vary or be constant along the length of radiating element 112. Further, the cross section of an antenna dielectric on any portion of radiating element 112 may not be symmetric. The various configurations of the antenna dielectric are designed to achieve the desired ablation profile as well as achieve the desired impedance matching for increased power efficiency. In an alternate embodiment, entire radiating element 112 is covered with a single dielectric. In one such embodiment, the layer of dielectric used to encapsulate the distal most portion of radiating element 112 may be thinner than the layer of dielectric used to coat the middle portion of radiating element 112.

Figure 1C:
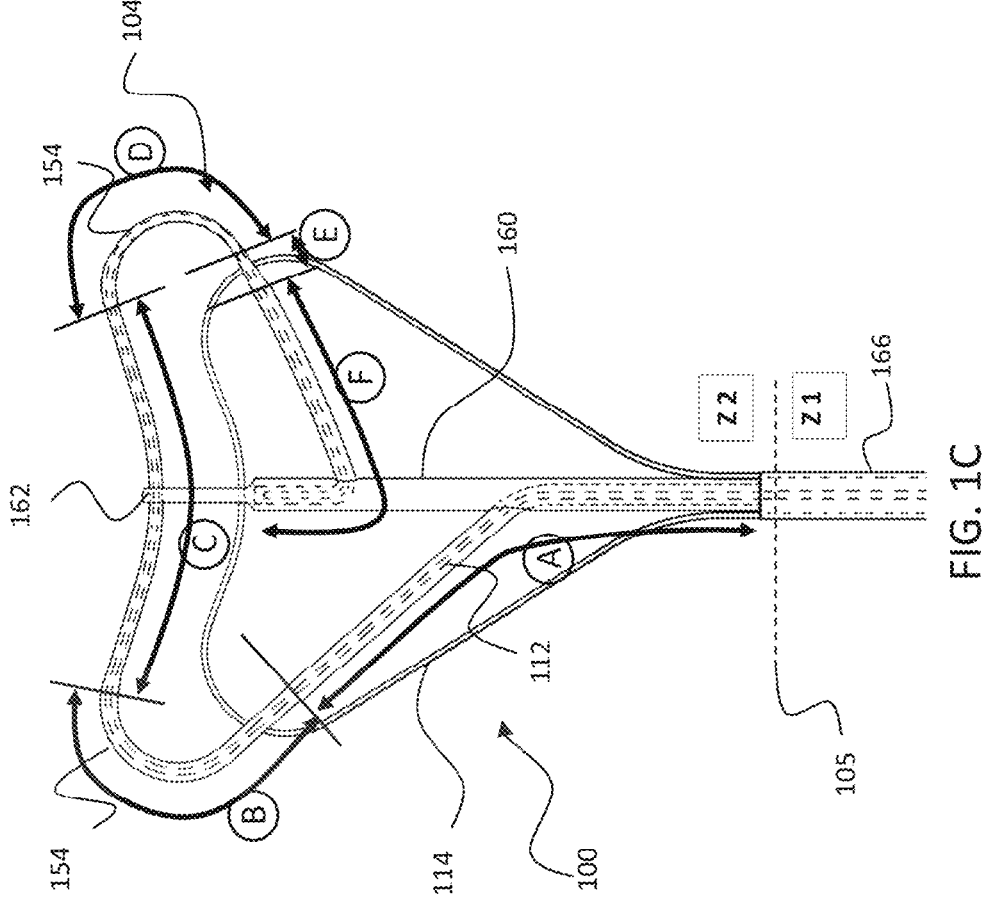
FIG. 1C shows a variation of an antenna comprising multiple dielectric layers around the outer loop.

FIG. 1C shows an embodiment of an antenna comprising multiple dielectric layers around radiating element 112. In this embodiment, transmission line jacket 166 is a layer of PEEK. Radiating element 112 is covered with various antenna dielectrics 116. Antenna dielectric 116 in region A is a layer of ePTFE with or without one or more layers of a polyolefin. Antenna dielectric 116 in region B is one or more layers of a polyolefin. Antenna dielectric 116 in region C is one or more layers of a polyolefin. Antenna dielectric 116 in region D is one or more layers of a polyolefin. Antenna dielectric 116 in region E is one or more layers of a polyolefin. Antenna dielectric 116 in region F is one or more layers of a polyolefin. As discussed elsewhere, various antenna dielectrics 116 covering radiating element 112 may be of different materials or have different material properties and/or dimensions.

In one device embodiment, radiating element 112 is made of a metallic material and the circumference of the metallic material of the distal region of radiating element 112 is more than the circumference of the metallic material of the middle portion of radiating element 112. This causes the dielectric to stretch more at the distal portion than at the middle portion of radiating element 112. This in turn generates a thinner layer of antenna dielectric at the distal portion of radiating element 112 than at the middle portion of radiating element 112. In another embodiment, entire radiating element 112 is made from a single length of metallic wire of a uniform cross section. In this embodiment, a tubular piece of dielectric of varying thickness is used to cover radiating element 112. The tubular dielectric is used to cover the distal and middle portions of radiating element 112 such that the layer of dielectric is thinner near the distal portion and thicker near the middle portion of radiating element 112.

In FIG. 1A, the shape of radiating element 112 is different from the shape of shaping element 114. Further, in FIG. 1A, radiating element 112 and shaping element 114 are substantially planar and the plane of radiating element 112 is substantially parallel to the plane of shaping element 114. Further, in FIG. 1A, both radiating element 112 and shaping element 114 are non-linear. However, one or more of radiating element 112 and shaping element 114 may comprise one or more linear regions. In the embodiment shown in FIG. 1A, radiating element 112 comprise a proximal linear region (at the proximal region of the antenna), a distal linear region (at the distal end of radiating element 112), and a middle non-linear region between the proximal linear region and the distal linear region. Proximal linear region distal linear region and antenna axis 168 are parallel to each other and are collinear. Distal linear region (at the distal end of radiating element 112) points in the distal direction.

In alternate embodiments, radiating element 112 and shaping element 114 may be substantially planar and the plane of radiating element 112 may be substantially non-parallel to the plane of shaping element 114. In alternate embodiments, radiating element 112 and shaping element 114 may be substantially non-planar. Examples of non-planar shapes include, but are not limited to: one or more splines, curves, loops, and two or more planar elements arranged in a non-planar configuration. As seen in FIG. 1A, the width of radiating element 112 is slightly larger than the width of shaping element 114. Embodiments similar to the one shown in FIG. 1A may be designed wherein the width of shaping element 114 is 100+/−50% of the width of outer loop 112. More specifically, embodiments similar to the one shown in FIG. 1A may be designed wherein the width of center loop 114 is 100+/−25% of the width of outer loop 112. Radiating element 112 is wider at the distal region of antenna 104 and is narrower at the proximal region of antenna 104. Similarly, shaping element 114 is wider at the distal region of antenna 104 and is narrower at the proximal region of antenna 104. Portions of radiating element 112 and shaping element 114 are parallel to each other. For example, in FIG. 1A, significant portions of radiating element 112 and shaping element 114 are parallel to each other at the distal end of antenna 104. This allows stronger coupling of the microwave field emitted by radiating element 112 to shaping element 114, thereby creating a region of high microwave field intensity (and thus deeper ablation) at the distal end of antenna 104. Also, the distal tip of radiating element 112 is located close to a portion of shaping element 114 as seen in FIG. 1A. This in turn creates a region of high microwave field intensity (and thus deeper ablation) at the distal end of antenna 104.

The two proximal ends of shaping element 114 may be electrically connected to the shielding element of transmission line 102. In the embodiments wherein the transmission line is a coaxial cable, two proximal ends of shaping element 114 are in electrical contact with two regions on outer conductor 106. In one embodiment, the two proximal ends of shaping element 114 are electrically connected to diametrically opposite regions on or near the distal end of outer conductor 106 such that shaping element 114 is located distal to the distal end of the transmission line 102 (in zone Z2). In one embodiment, the two proximal ends of shaping element 114 are soldered to the distal end of outer conductor 106. In another embodiment, the two proximal ends of shaping element 114 are laser welded to the distal end of outer conductor 106. In another embodiment, the proximal ends of shaping element 114 are passed through holes in a molded flange located on the proximal portion of dielectric 160, and then connected to the outer conductor layer of the coaxial cable using a heat shrink tubing to securely hold them in place. A portion of the outer conductor layer of the coaxial cable which is in contact with the proximal ends of shaping element 114 may utilize a conductive metal tube (such as copper) to cover the outer conductor wires (braids or strands). In another embodiment the proximal ends of shaping element 114 are connected to the outer conductor layer of the coaxial cable using crimping. The two proximal ends of shaping element 114 may be connected to the distal end of outer conductor 106 in various configurations including, but not limited to lap joint and butt joint. In an alternate embodiment, at least one of the two proximal ends of shaping element 114 is not connected to the distal end of outer conductor 106. For example, at least one of the two proximal ends of shaping element 114 may be electrically connected to a region of outer conductor 106 that is proximal to the distal end of outer conductor 106. In one embodiment, the two proximal ends of shaping element 114 are tucked inside the distal end of outer jacket 118. In this embodiment, the proximal end of dielectric piece 160 pushes against the two proximal ends of shaping element 114. In this and other embodiments, the two proximal ends of shaping element 114 are held in place by friction. A transmission line jacket 166 may be located over a part of or the entire portion of the transmission line 102 (e.g. a coaxial cable 102) that connects to antenna 104. The distal end of transmission line jacket 166 may be located near the two proximal ends of shaping element 114. Transmission line jacket 166 may be made of sufficiently stiff materials including, but not limited to:

Polyether ether ketone (PEEK), Polyether block amide (PEBA) e.g. PEBAX®, fluorinated ethylene propylene (FEP), fluoropolymers, polyurethanes, etc. that increase the stiffness of the transmission line. This in turn allows the user to obtain force feedback during the procedure as described earlier. Also, a stiff transmission line jacket 166 facilitates the pushing or pulling or turning of the device during a procedure by a user.

Figure 2B:
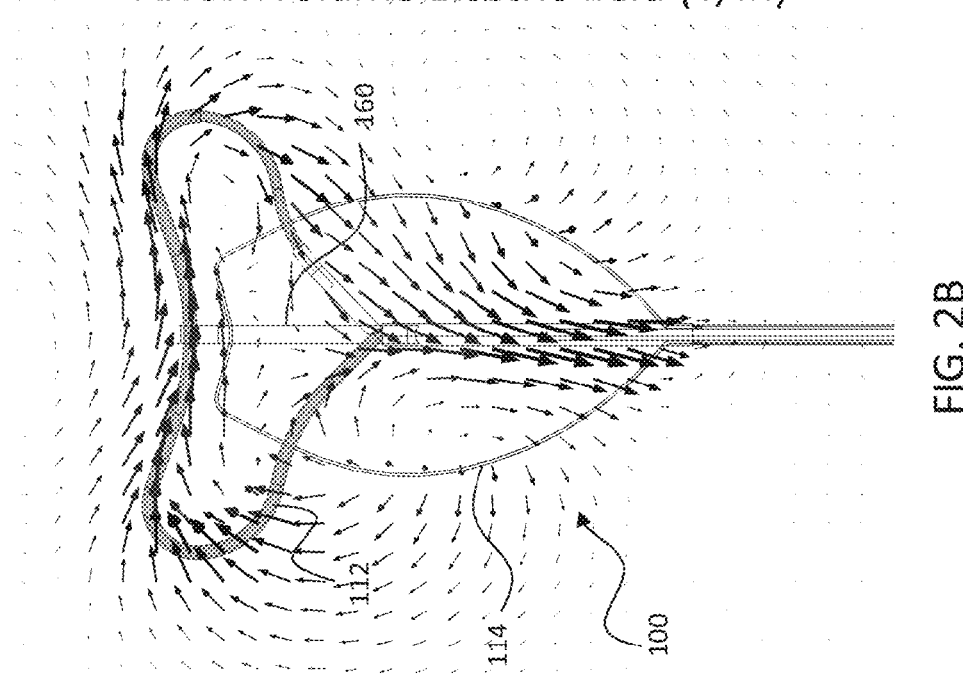
FIGS. 2B, 3B, and 4B show front views of the electromagnetic field profile generated by the antenna of FIG. 1B.
Figure 2A:
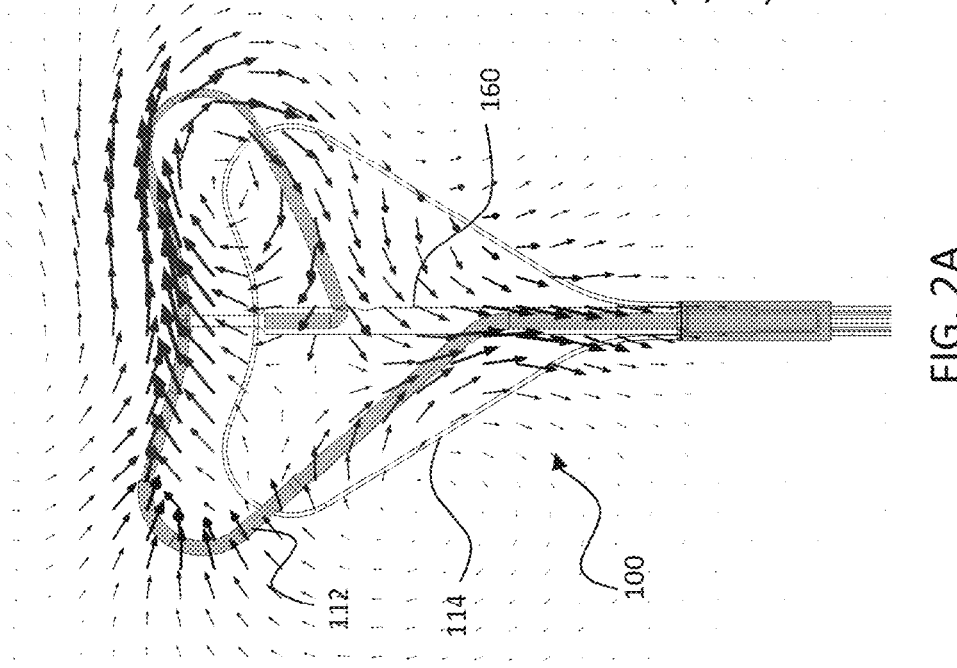
FIGS. 2A, 3A, and 4A show front views of the electromagnetic field profile generated by the antenna of FIG. 1A.
Figure 3A:
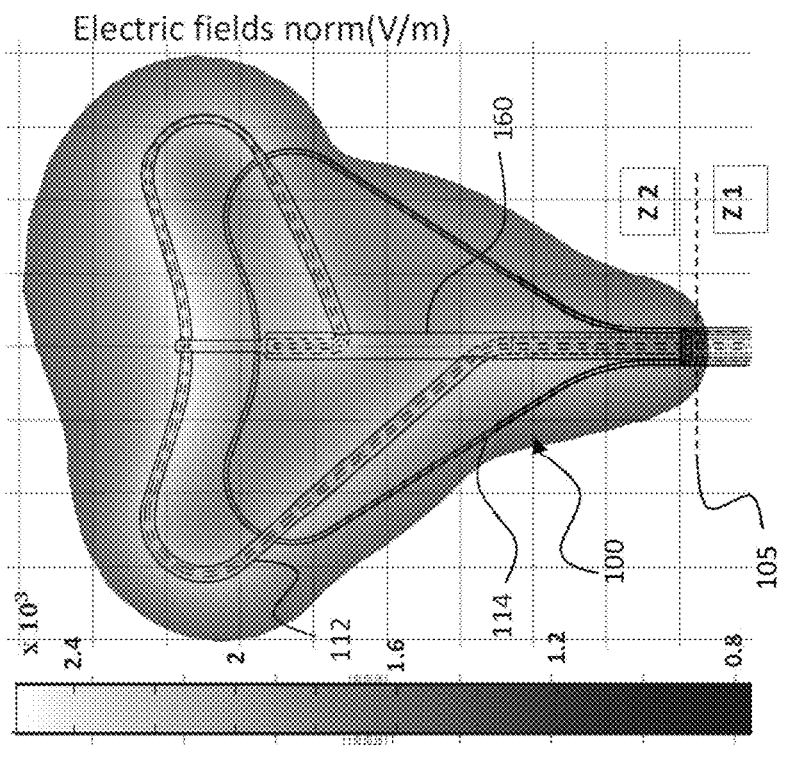
Figure 4B:
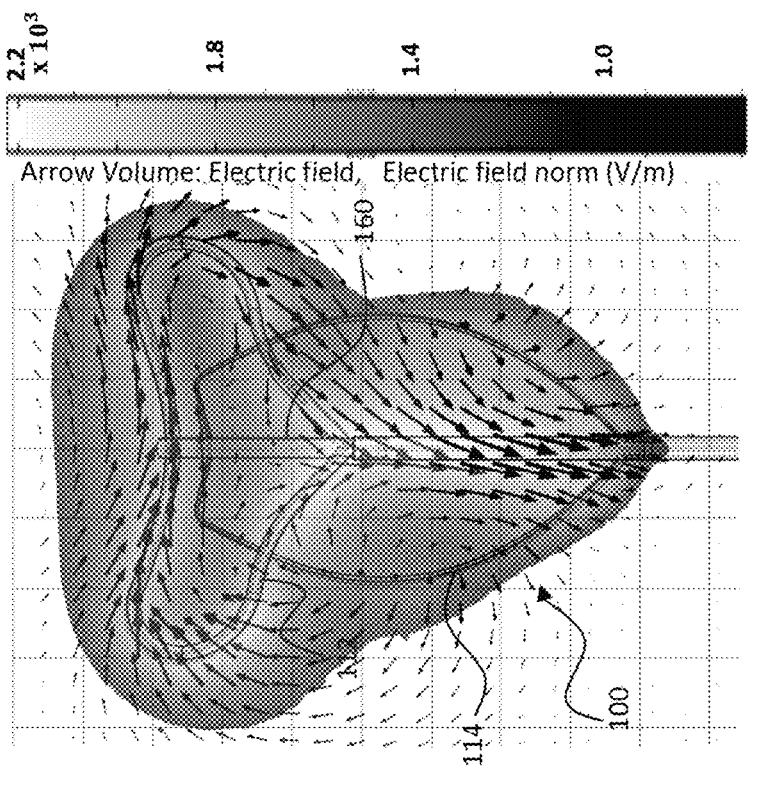
Figure 4A:
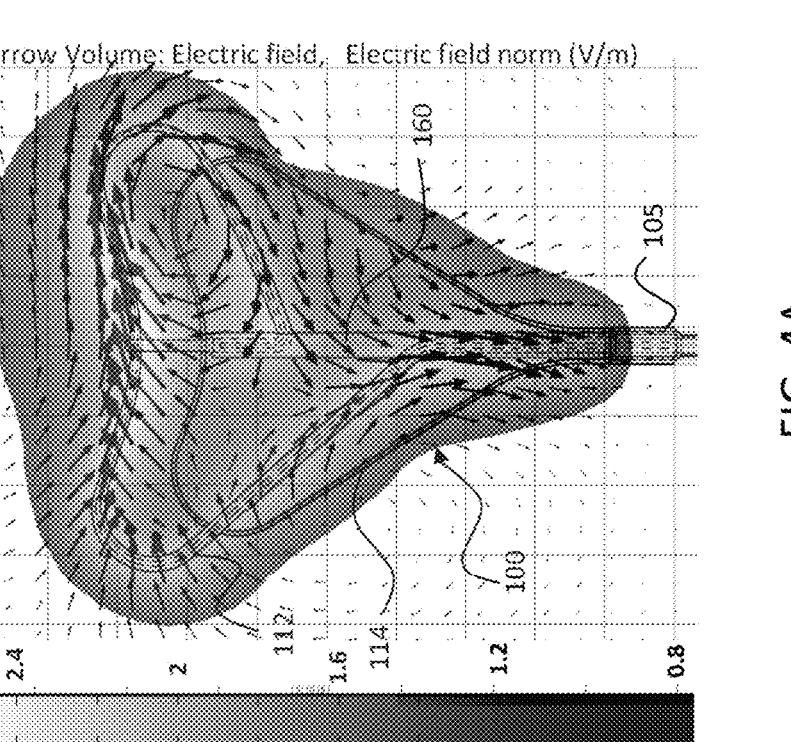

In a method embodiment, when ablation system 100 is used for endometrial ablation, antenna 104 of FIG. 1A generates a microwave field that is more concentrated towards the fundus and is less concentrated towards the cornua and towards the cervix as shown in FIGS. 2A, 3A, 4A, and 5A. Thus, the depth of ablation generated by antenna 104 is deeper at the fundus and is less deep towards the cornua and towards the cervix. Such a profile is clinically desired for improved safety and efficacy. Such an ablation profile thoroughly ablates endometrium near the fundus and cornua. This in turn lowers the risk of hematometra or trapped menstrual blood in the uterine cavity. In one embodiment, the ablation profile is shaped to ablate a majority of the basalis layer of the uterine endometrium. In one embodiment, shaping element 114 is made of a round or flat wire. Examples of wires that can be used to make shaping element 114 are wires made of silver or gold plated or clad or drawn filled tubes of Nitinol or stainless steel. In one embodiment, the wire used to make shaping element 114 has a cross sectional profile of about 0.025"×about 0.007". In one embodiment, shaping element 114 is made of a wire of round cross section with two flattened ends and a central flattened portion. In one such embodiment, shaping element 114 is made of a silver or gold clad Nitinol or stainless-steel wire with a circular cross-sectional profile and a diameter of 0.01"+/−0.005". The wire may comprise two flattened ends and a central flattened portion with a cross sectional dimensions of 0.011"+/−0.005" by 0.007"+/−0.003". Such loop shaped shaping elements 114 do not act as a shield for the microwave field. This non-shielding action is visible in FIGS. 2A, 3A, and 4A. FIGS. 2A, 3A, and 4A show that there is no sharp drop in the microwave field intensity past shaping element 114. In the embodiment of FIG. 1A, shaping element 114 is roughly heart shaped with two distal rounded lobes and a narrower proximal region. Two proximal ends of shaping element 114 are electrically attached to two diametrically opposite regions of the outer conductor of coaxial cable 102. In the embodiment of FIG. 1A, the width of shaping element 114 is 20+/−10 mm and the longitudinal length of deployed shaping element 114 measured along the axis of coaxial cable 102 from line 105 till the distal most region of shaping element 114 is 33+/−10 mm. When ablation system 100 is used for endometrial ablation, radiating element 112 and shaping element 114 both contact the endometrial tissue surface.

Shaping element 114 may be mechanically independent from radiating element 112 or may be mechanically attached to radiating element 112. In the embodiment shown in FIG. 1A, shaping element 114 and radiating element 112 are both mechanically connected to dielectric piece 160. In an alternate embodiment, a portion of shaping element 114 passes through the interior of radiating element 112 through second distal opening 176. In an alternate embodiment, a portion of shaping element 114 is mechanically connected to radiating element 112. This may be done for example, by using an adhesive to connect a portion of shaping element 114 to radiating element 112. In an alternate embodiment, one or more portions of shaping element 114 are mechanically connected to one or more portions of radiating element 112 by one or more flexible attachments.

Parts of shaping element 114 may or may not be covered by one or more layers of antenna dielectric materials 116. In the embodiment of FIG. 1A, one or more or all metallic surfaces of shaping element 114 are exposed to the device environment.

Portions of radiating element 112 and shaping element 114 may be made from one or more of lengths of metals such as copper, Nitinol, aluminum, silver or any other conductive metals or alloys. One or more portions of radiating element 112 and shaping element 114 may also be made from a metallized fabric or plastics.

FIGS. 2A, 3A, and 4A show views of the electromagnetic field profile generated by the antenna of FIG. 1A. In the embodiment shown in FIGS. 2A, 3A, and 4A, shaping element 114 is not covered with any antenna dielectric 116. Thus, the metallic surface of shaping element 114 is exposed to the surrounding. Radiating element 112 and shaping element 114 may physically touch each other when deployed in the anatomy. The design of the antenna configuration shown provides a shaped electromagnetic field that is more concentrated towards the fundus and is less concentrated towards the cornua and towards the cervix. For example, the size of the arrows shown in FIG. 4A generally increase along the mid region of the radiating element 112, which is adjacent to the fundus of the uterus. The cornua of the uterus is adjacent to the rounded edges of the radiating element 112 and the cervix will be located towards the line 105. Thus, the depth of ablation generated by antenna 104 is deeper at the fundus and is less deep towards the cornua and towards the cervix. Also, the microwave field is shaped such that it is wider distally and narrower proximally. Such a microwave field shape is clinically desirable for endometrial ablation. Also, FIGS. 2A, 3A, and 4A show that the microwave field volumetrically envelops the entire antenna 104 and is substantially bilaterally symmetric.

Figure 4C:
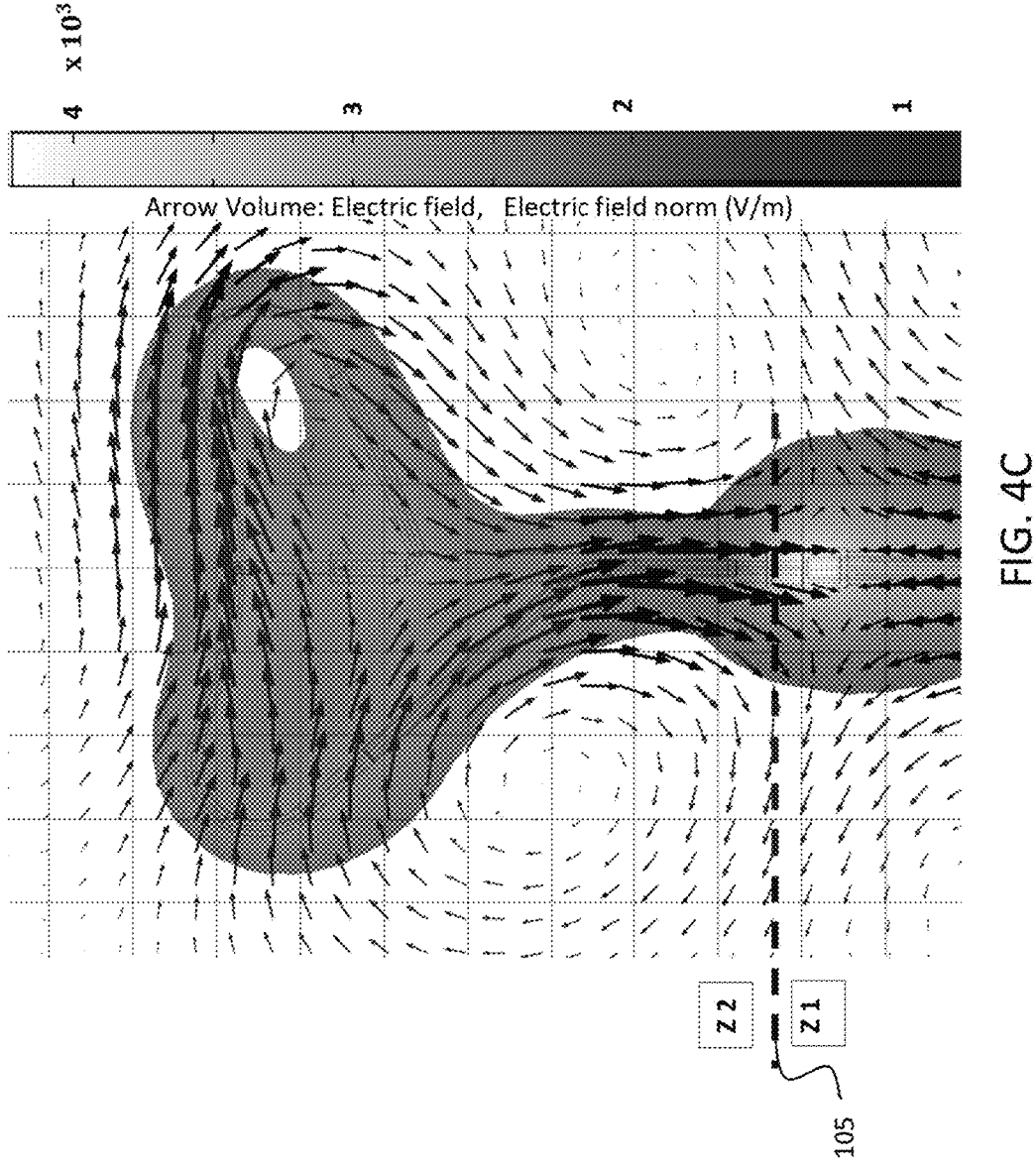
FIG. 4C shows the front view of the electromagnetic field profile generated by the antenna of FIG. 1A without a center loop.

FIG. 4C shows the front view of the electromagnetic field profile generated by an antenna similar to FIG. 1A but without shaping element 114. The microwave effect of shaping element 114 in FIG. 1A can be seen by comparing FIG. 4A to FIG. 4C. FIG. 4C shows a first unshaped field (without being shaped by any shaping element). As shown, there is a concentration of the field towards to top right of the antenna and along the line 102, where the field intensity correlates to the size of the arrows. When the antenna 104 comprises a shaping element 114 as shown in FIG. 1A, the antenna generates a shaped microwave field as shown in FIG. 4A.

It should be noted that in FIGS. 2A, 3A, and 4A, the shaped microwave field is more uniformly distributed over a wider area of the endometrium than in FIG. 4C. In FIG. 4C, the unshaped microwave field is more concentrated near the distal end of coaxial cable 102. A more uniformly distributed, shaped microwave field such as in FIGS. 2A, 3A, and 4A is clinically desirable for endometrial ablation. Further when antenna 104 of FIG. 1A is used for endometrial ablation, the microwave field is distributed over a wider area of the endometrium that the microwave field generated by antenna 104 of FIG. 4C. This can be seen by comparing the field distal to the distal end of coaxial cable 102 in FIGS. 2A, 3A, and 4A to the field distal to the distal end of coaxial cable 102 in FIG. 4C. Further, in FIG. 4C, a portion of the unshaped microwave field extends to a significant distance proximal to the distal end of coaxial cable 102. In FIGS. 2A, 3A, and 4A, an insignificant portion of the microwave field extends proximally to the distal end of coaxial cable 102.

In the embodiment of FIGS. 1A and FIGS. 2A, 3A, and 4A, the nearest conductive path is provided by the conductive shaping element 114 instead of the shielding element (e.g. outer conductor 106) of transmission line 102 at the distal region of the transmission line 102.

The presence of shaping element 114 has prevented the microwave field from coupling to the distal region of the transmission line 102. Virtually none of the microwave field is located around the distal region of transmission line 102. Further, since a vast majority of the emitted microwave field is deposited in zone Z2, the power deposition of antenna 104 is improved. Virtually no portion of the field is wasted in zone Z1. Thus, the microwave field profile of FIGS. 2A, 3A, and 4A is advantageous over the microwave field profile of FIG. 4C since it limits collateral damage to healthy tissue. Thus, the presence of shaping element 114 shapes the microwave field such that the microwave field is more distributed. In absence of shaping element 114, the microwave field interacts with an element of transmission line 102 such as the outer conductor of a coaxial cable. This creates non-desirable profile of the microwave field e.g. a concentrated field around the distal region of the transmission line 102 as shown in FIG. 4C. This interaction can also cause backward heating of coaxial cable 102 that may lead to collateral damage of healthy tissue. Further, the combination of radiating element 112 and shaping element 114 creates a more robust antenna 104 wherein the performance of antenna 104 is less affected by distortions during clinical use. Also, FIGS. 2A, 3A, and 4A show that the microwave field volumetrically envelops entire antenna 104.

Figure 5B:
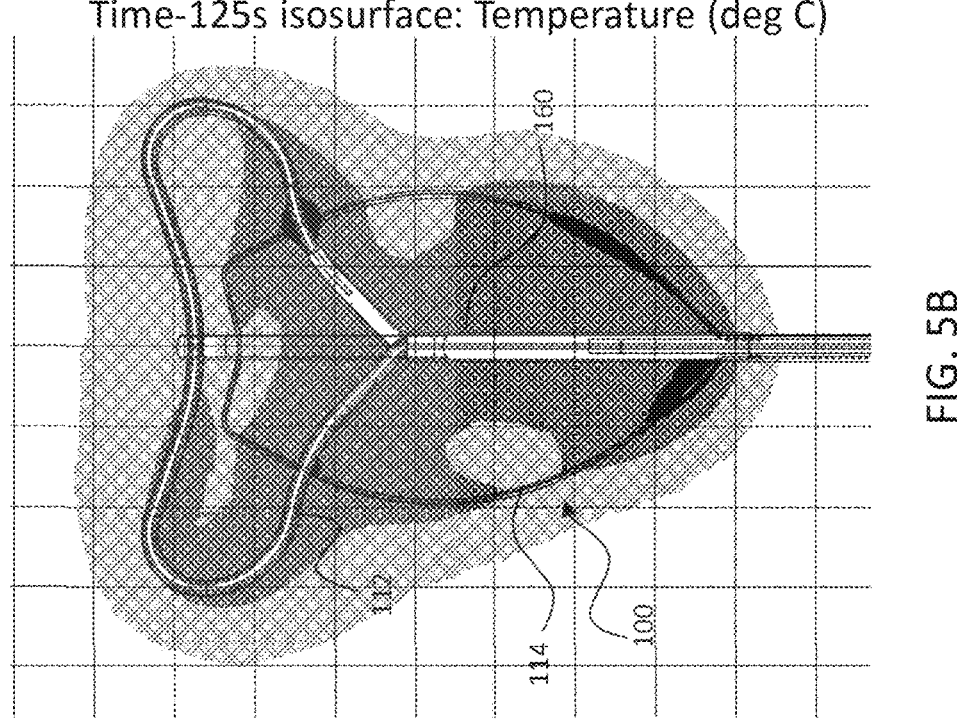
FIGS. 5B and 5D show the front and side views respectively of the thermal profile of the antenna of FIG. 1B.
Figure 5A:
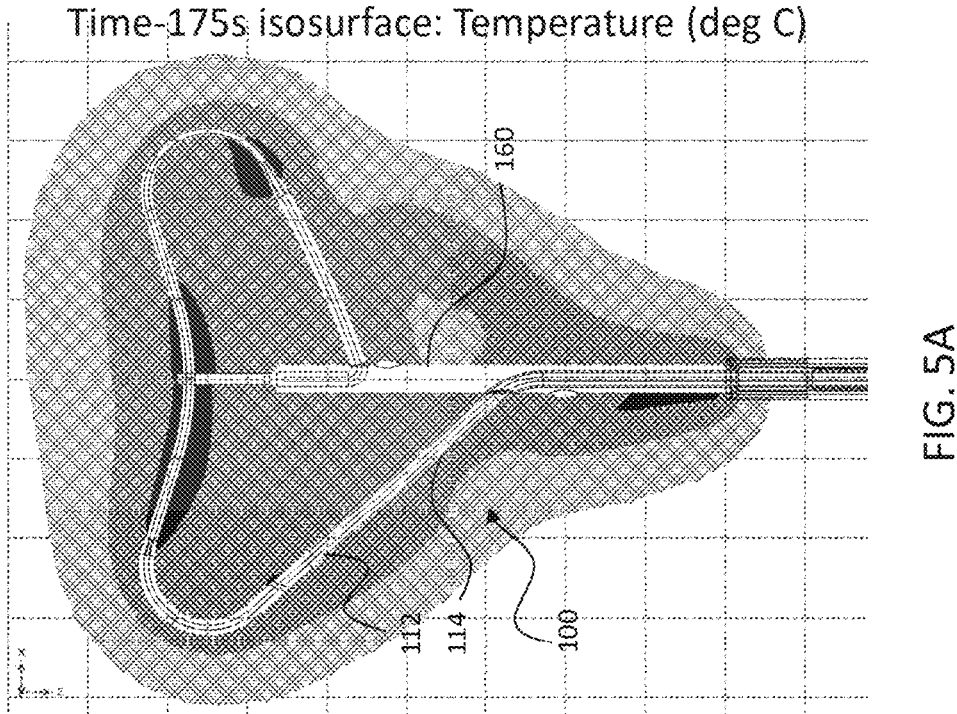
FIGS. 5A and 5C show the front and side views respectively of the thermal profile of the antenna of FIG. 1A.
Figure 5D:
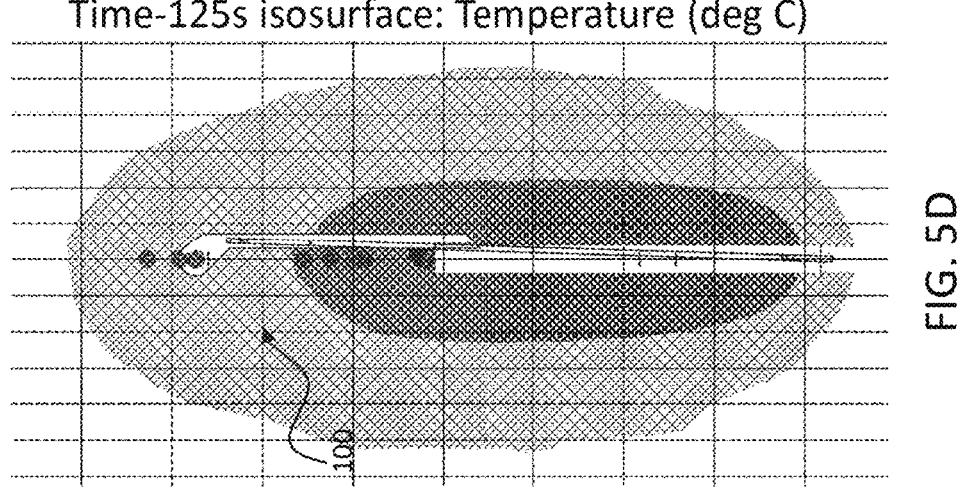
Figure 5C:
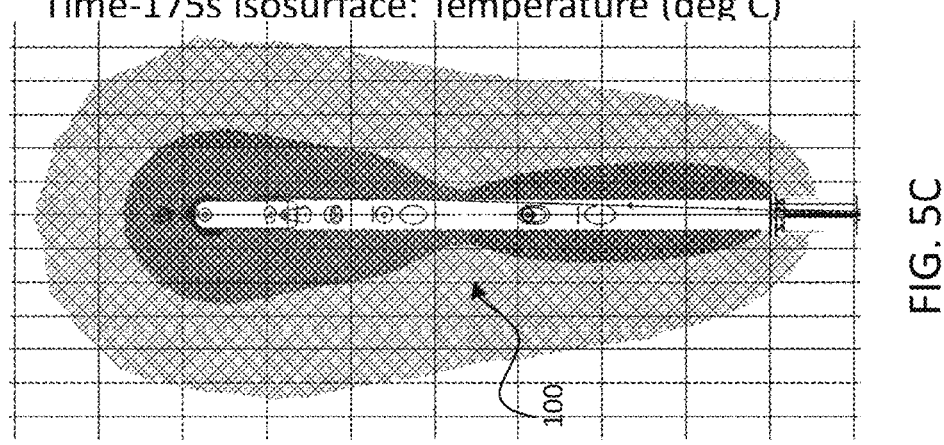

FIGS. 5A and 5C show front and side views respectively of the thermal profile of the antenna of FIG. 1A. In FIGS. 5A and 5C, the outer boundary of the light gray colored zone shows the 50 Celsius isotherm. The outer boundary of the dark gray colored zone shows the 70 Celsius isotherm. The outer boundary of the black colored zone shows the 100 Celsius isotherm. Similar color code is used for FIGS. 5B and 5D. The thermal profile of FIGS. 5A and 5C show that when antenna 104 is inserted into the uterine cavity and used for ablating the endometrium, the fundal region will show the maximum ablation depth. The ablation zone will taper towards the lower uterine region and the cornua.

Further, the electrical field profile of FIGS. 2A, 3A, and 4A and the thermal profile of FIGS. 5A and 5C demonstrates that the entire uterine endometrium can be ablated in a single ablation. Thus, the physician does not need to reposition antenna 104 after a first endometrial ablation. This novel aspect of the device and procedure greatly reduces the amount of time needed for the procedure and also reduces the procedure risks and physician skill requirements. In the embodiments disclosed herein, a combination of direct microwave dielectric heating and thermal conduction through tissue is used to achieve the desired therapeutic effect. The thermal conduction evens out any minor variations in the microwave field and enables the creation of a smooth, uniform ablation. Further, the electrical field profile of FIGS. 2A, 3A, and 4A and the thermal profile of FIGS. 5A and 5C demonstrates that antenna 104 is capable of ablating an entire volume surrounding antenna 104 not just ablating between the surfaces of radiating element 112 and shaping element 114. Further, the electrical field profile of FIGS. 2A, 3A, and 4A and the thermal profile of FIGS. 5A and 5C demonstrates that antenna 104 is capable of ablating a tissue region without leaving any "gaps" of unablated tissue within that tissue region. Further, the electrical field profile of FIGS. 2A, 3A, and 4A and the thermal profile of FIGS. 5A and 5C demonstrates that the entire microwave field generated by antenna 104 is used for ablation. The entire microwave field comprises the microwave field around radiating element 112, the microwave field around shaping element 114, the microwave field between radiating element 112 and shaping element 114 and the field within shaping element 114. Further, the electrical field profile of FIGS. 2A, 3A, and 4A and the thermal profile of FIGS. 5A and 5C demonstrates that the microwave field is located all around radiating element 112 and is not shielded or reflected by shaping element 114. Thus, shaping element 114 does not act as a shield or reflector in the embodiment shown in FIG. 1A.

Figures 6A, 6B:
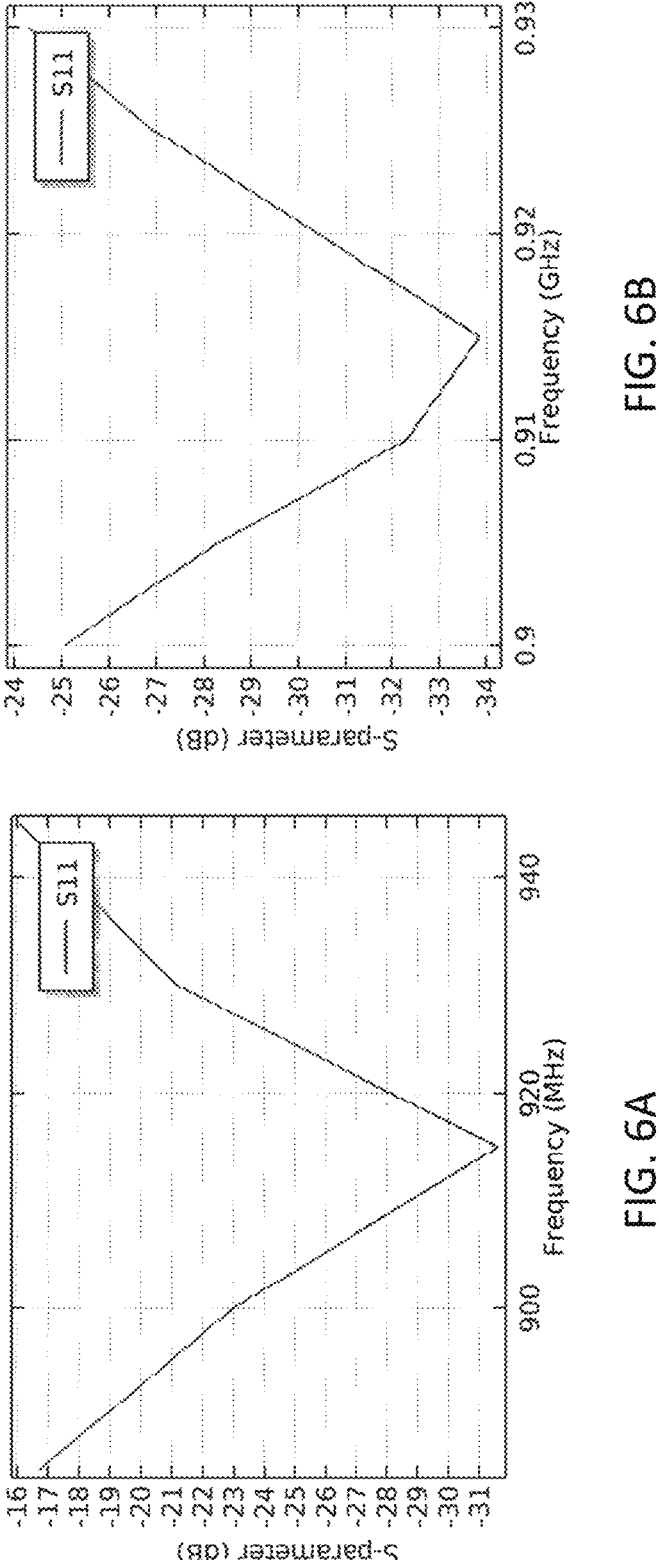
FIG. 6A shows the simulated return loss of an ablation device with the antenna of FIG. 1A.
FIG. 6B shows the simulated return loss of an ablation device with the antenna of FIG. 1B.
Figure 6C:
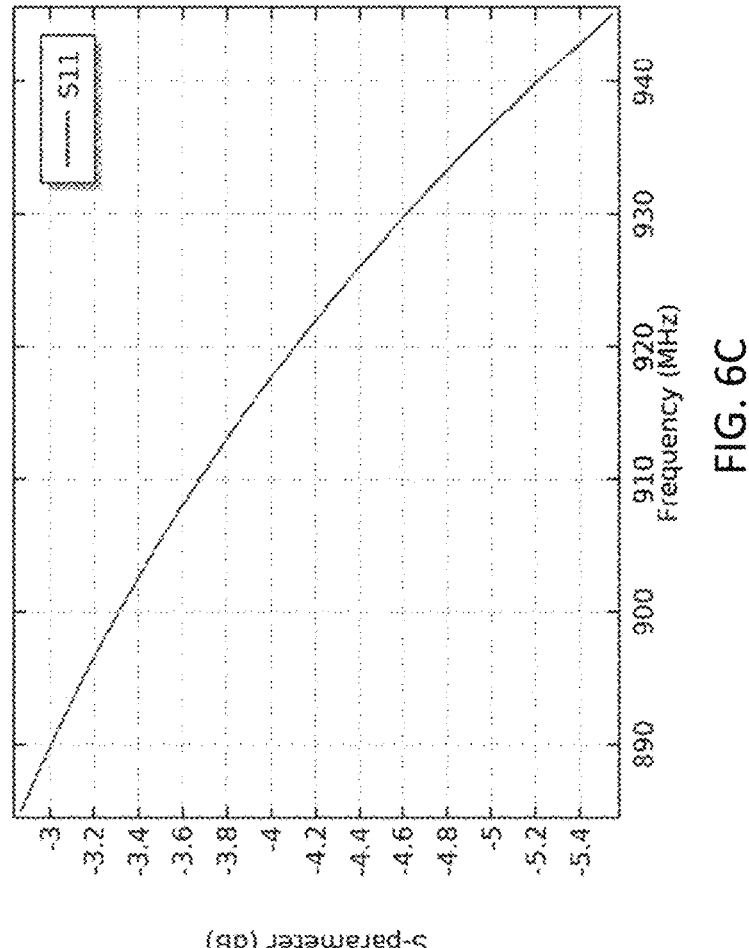
FIG. 6C shows the simulated return loss of an ablation device with the antenna of FIG. 1A without a center loop.

FIG. 6A shows the simulated return loss of antenna 104 of FIG. 1A. The simulated return loss of antenna 104 of FIG. 1A (solid line) shows good matching (<−30 dB) at 915 MHz. The simulated return loss of an ablation device with an embodiment of antenna 104 without shaping element 114 shows a return loss of about −4 dB at 915 MHz (See FIG. 6C). Thus, the presence of shaping element 114 also improves the matching, reduces the return loss and increases the power efficiency. In the presence of shaping element 114, microwave power is delivered more efficiently to the tissue and not wasted as heat generated within ablation system 100.

Shaping element 114 can also increase the frequency range (bandwidth) over which antenna 104 delivers an acceptable performance. Thus, a larger frequency range (bandwidth) is available over which antenna 104 delivers an acceptable performance. This in turn allows for a design of antenna 104 wherein minor distortions of antenna 104 during typical clinical use or due to minor manufacturing variations do not significantly affect the performance of antenna 104.

To highlight the features of the improved devices an antenna similar to the antenna disclosed in US patent application publication no. 2011/0004205 is shown for comparison in FIG. 1B. FIGS. 2B, 3B, and 4B show the front views of the electromagnetic field profile generated by the antenna of FIG. 1B. FIGS. 5B and 5D show the front and side views respectively of the thermal profile of the antenna of FIG. 1B. FIG. 6B shows the simulated return loss of an ablation device with antenna 104 of FIG. 1B.

FIG. 7A shows the design details of a first variation of an antenna. FIG. 7A shows an embodiment of antenna 104 wherein the distal end of radiating element 112 is covered with a thick antenna dielectric 116. Antenna dielectric 116 immediately proximal to this region is thinner (i.e., around the corner region 154). The corner region 154 shown is covered with the thinnest layer of antenna dielectric seen in FIG. 7A. This design of antenna dielectric 116 covering radiating element 112 may be achieved, for example, using multiple layers of one or more dielectric materials.

FIGS. 7B, 7C, and 7D show the electromagnetic field shape, location of hot spots (high temperature zones), and the matching of the antenna of FIG. 7A. FIG. 7B shows that the electromagnetic field generated by the antenna of FIG. 7A has a roughly triangular shape that approximates the shape of the uterine cavity and is especially suited for endometrial ablation. FIG. 7C shows the location of the 100 degree Celsius zones. There is a large hot spot at the fundus and two hot spots at the regions where radiating element 112 crosses shaping element 114. FIG. 7D shows good matching (about −28 dB) at 915 MHz frequency.

Figures 7E, 7F, 7G:
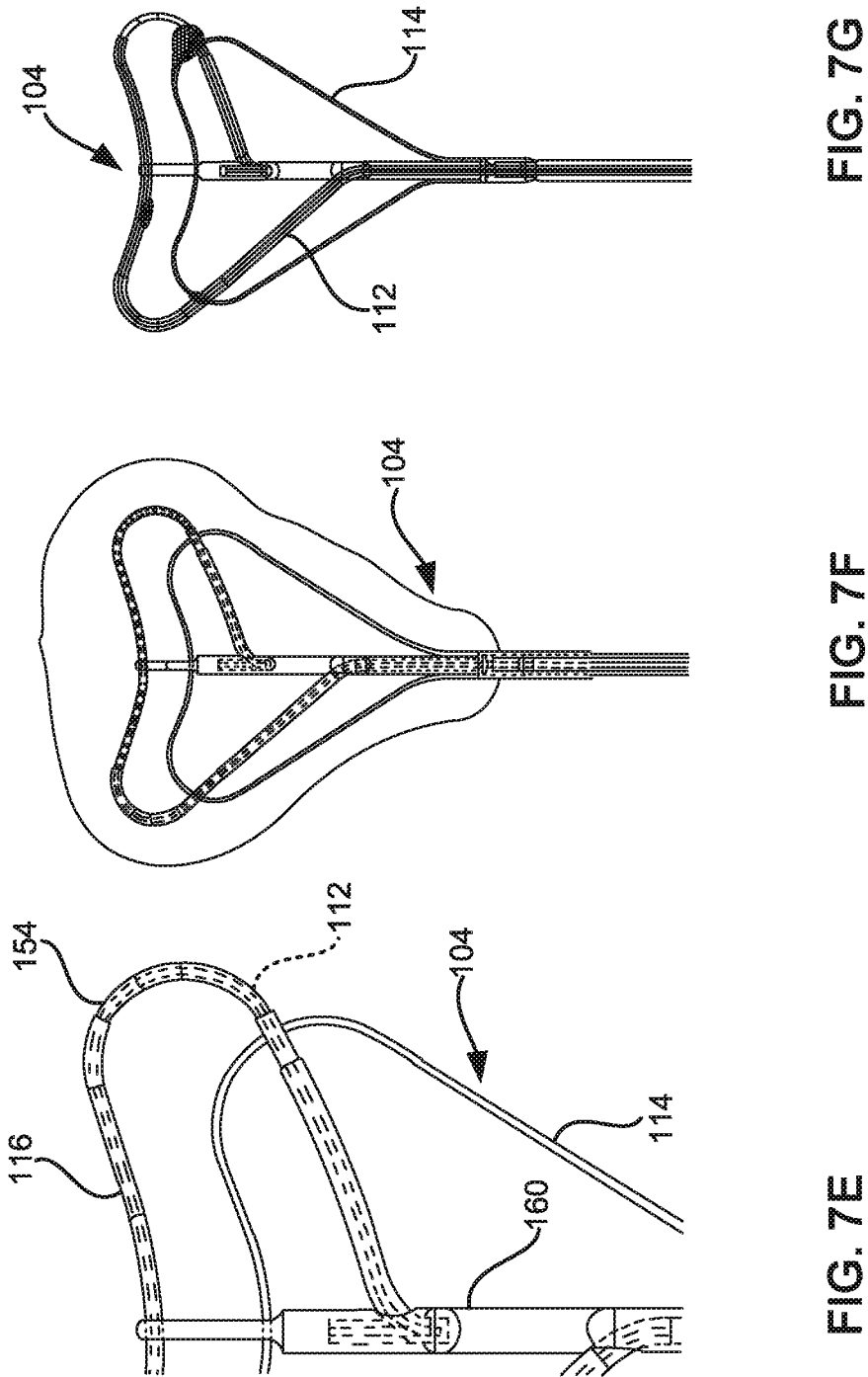

FIG. 7E shows the design details of a second variation of an antenna. The embodiment of FIG. 7E is similar to the embodiment of FIG. 7A, except for the sharp bend of radiating element 112 near the distal end of radiating element 112.

FIGS. 7F, 7G, and 7H show the electromagnetic field shape, location of hot spots, and the matching of the antenna of FIG. 7E. FIG. 7F shows that the electromagnetic field generated by the antenna of FIG. 7E has a roughly triangular shape that approximates the shape of the uterine cavity and is especially suited for endometrial ablation. FIG. 7G shows the location of the 100 degree Celsius zones. There is a small hot spot at the fundus and two hot spots (one large, one small) at the regions where radiating element 112 crosses shaping element 114. FIG. 7H shows good matching (about −29 dB) at 915 MHz frequency.

Figures 7I, 7J, 7K:
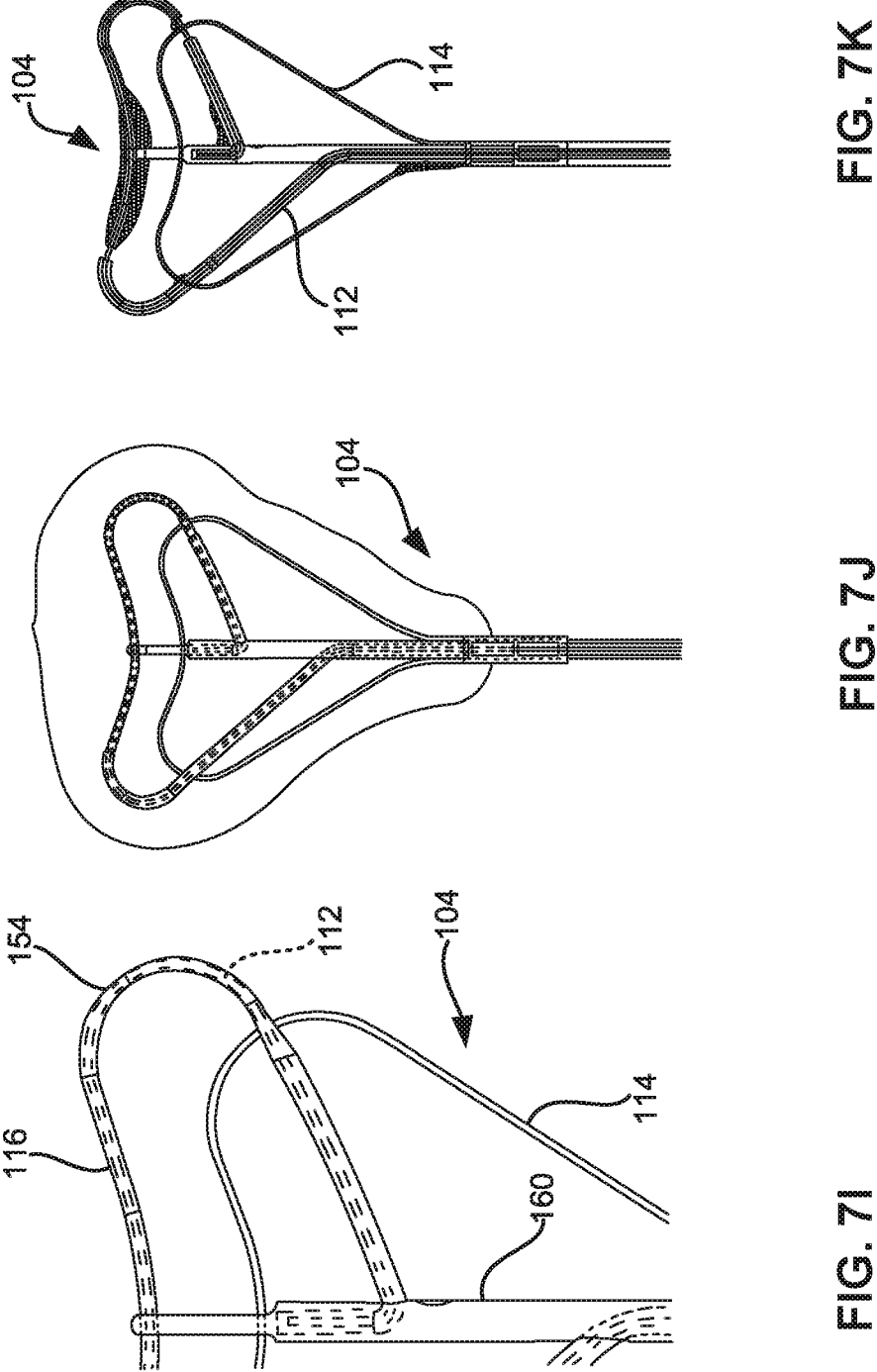

FIG. 7I shows the design details of a third variation of an antenna. FIG. 7I shows an embodiment of antenna 104 wherein the distal region of radiating element 112 is covered with an antenna dielectric 116 that is thinner at the corner region 154 shown. This design of antenna dielectric 116 covering radiating element 112 may be achieved, for example, using a single layer of dielectric material with varying thickness along its length.

FIGS. 7J, 7K, and 7L show the electromagnetic field shape, location of hot spots, and the matching of the antenna of FIG. 7I. FIG. 7J shows that the electromagnetic field generated by the antenna of FIG. 7I has a roughly triangular shape that approximates the shape of the uterine cavity and is especially suited for endometrial ablation. FIG. 7K shows the location of the 100 degree Celsius zones. There is a large hot spot at the fundus and four small hot spots as shown. FIG. 7L shows good matching (about −30 dB) at 915 MHz frequency.

Figures 7M, 7N, 7O:
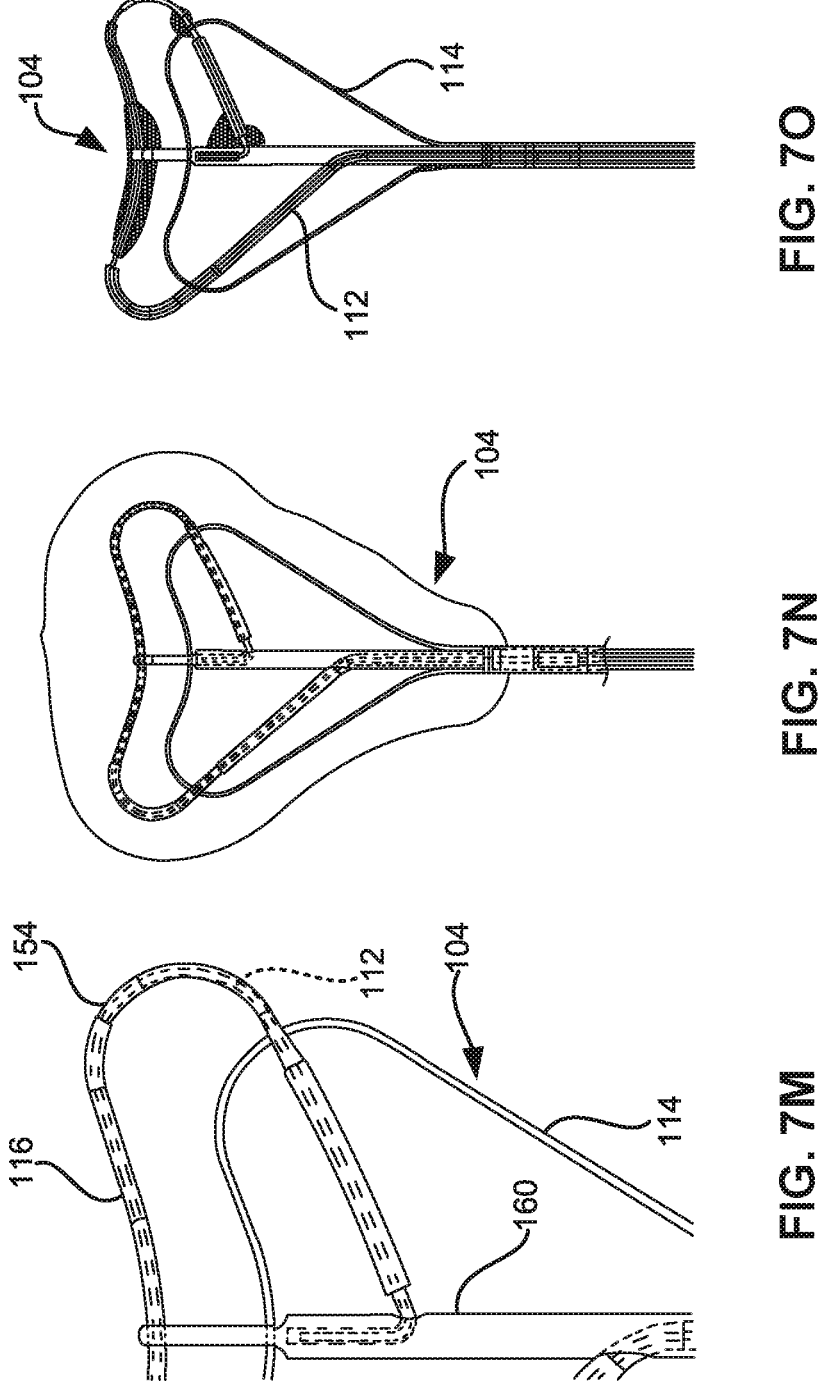

FIG. 7M shows the design details of a fourth variation of an antenna. The embodiment of FIG. 7M is similar to the embodiment of FIG. 7I, except that multiple dielectric materials are used to create the antenna dielectric 116 layer over radiating element 112.

FIGS. 7N, 7O, and 7P show the electromagnetic field shape, location of hot spots, and the matching of the antenna of FIG. 7M. FIG. 7N shows that the electromagnetic field generated by the antenna of FIG. 7M has a roughly triangular shape that approximates the shape of the uterine cavity and is especially suited for endometrial ablation. FIG. 7O shows the location of the 100 degree Celsius zones. There is a large hot spot at the fundus and three small hot spots as shown. FIG. 7P shows good matching (about −30 dB) at 915 MHz frequency.

Figures 7Q, 7R, 7S:
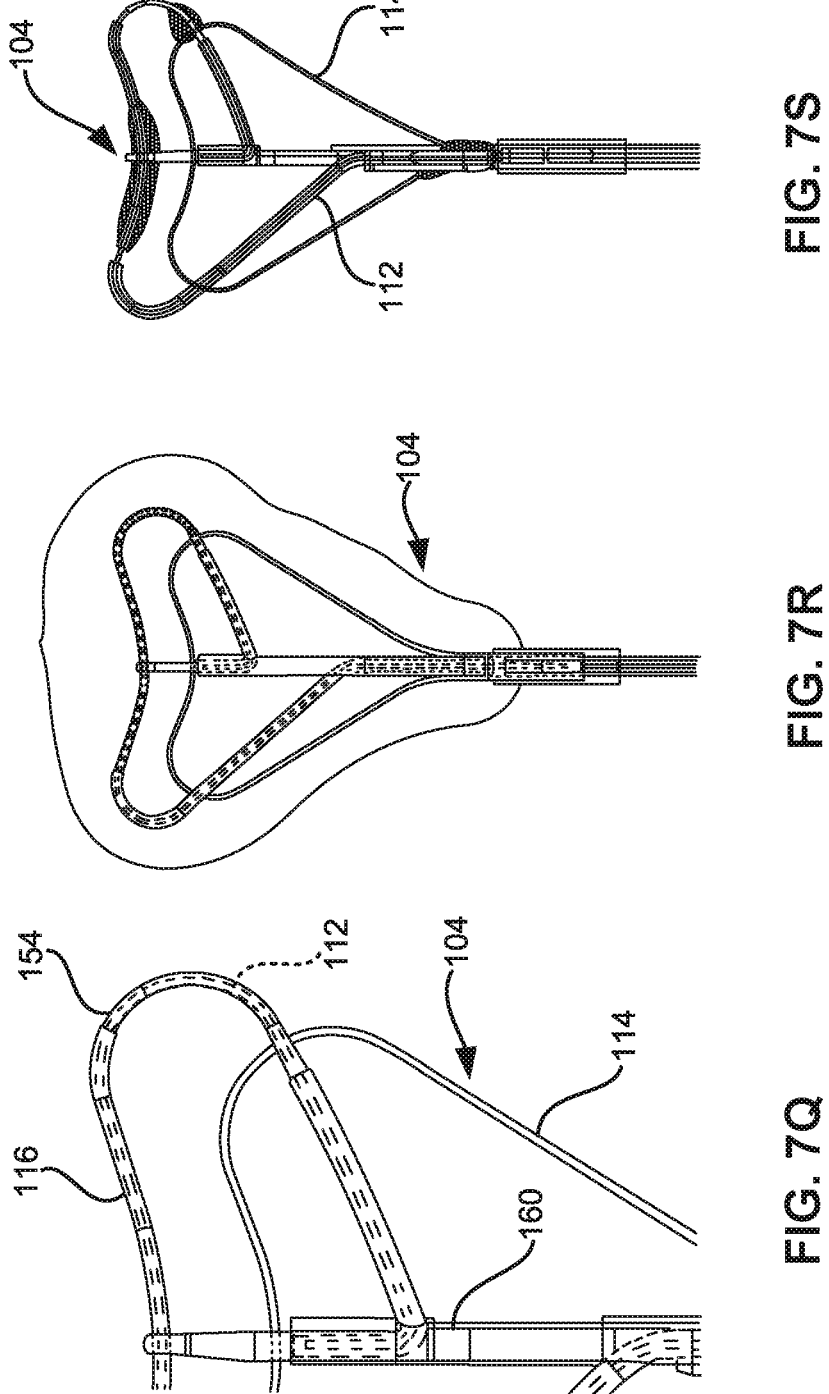

FIG. 7Q shows the design details of a fifth alternate embodiment of the present invention. The embodiment of FIG. 7Q is similar to the embodiment of FIG. 7M, except for the presence of an additional dielectric layer over the distal end of outer loop 112.

FIGS. 7R, 7S, and 7T show the electromagnetic field shape, location of hot spots, and the matching of the antenna of FIG. 7Q. FIG. 7R shows that the electromagnetic field generated by the antenna of FIG. 7Q has a roughly triangular shape that approximates the shape of the uterine cavity and is especially suited for endometrial ablation. FIG. 7S shows the location of the 100 degree Celsius zones. There is a large hot spot at the fundus and two small hot spots as shown. FIG. 7T shows good matching (about −27 dB) at 915 MHz frequency.

Figures 7U, 7V, 7W:
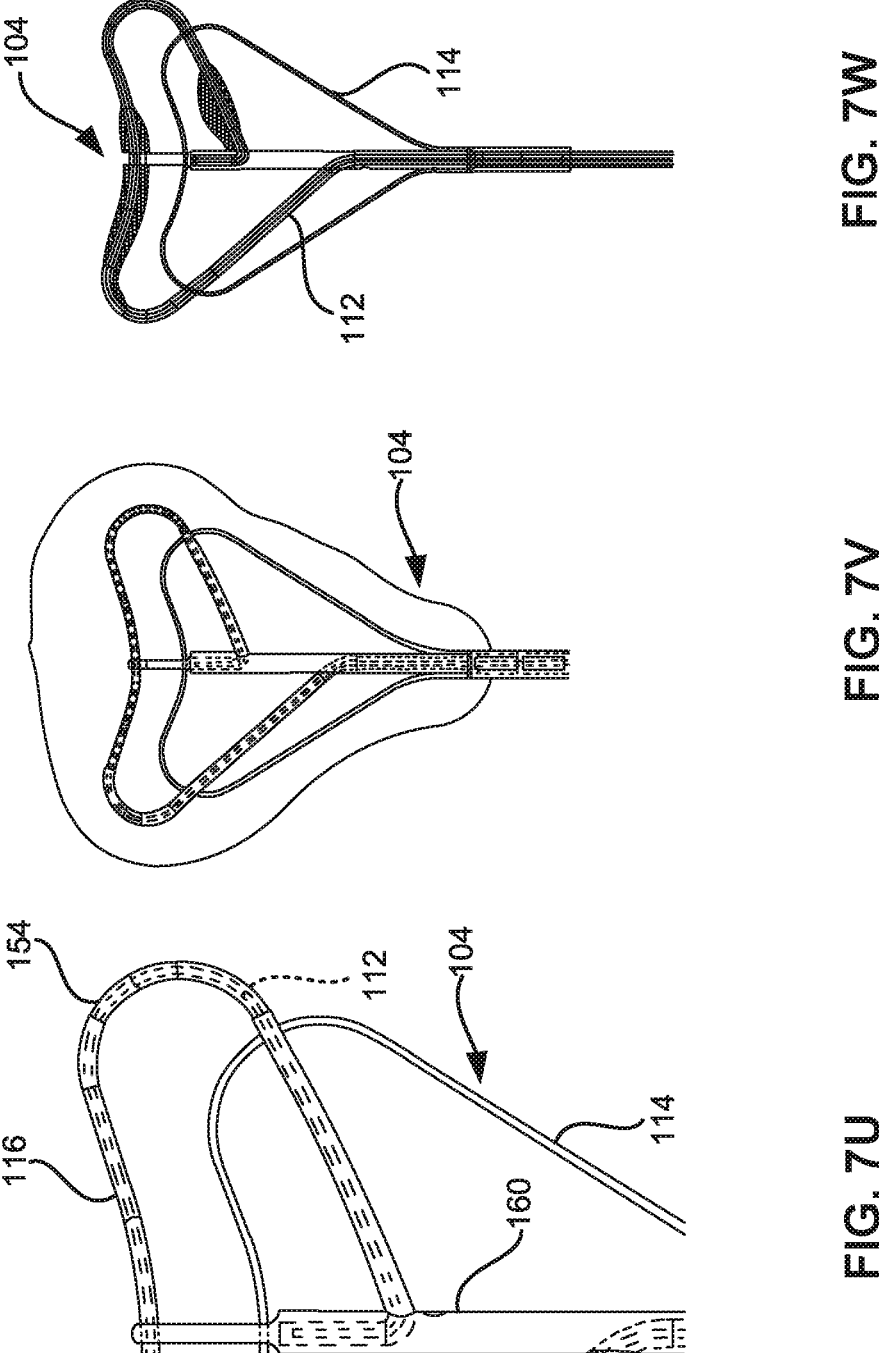
FIG. 7U shows the design details of another variation of an antenna.
FIGS. 7V, 7W, and 7X show the electromagnetic field shape, location of hot spots, and the matching of the antenna of FIG. 7U.

FIG. 7U shows the design details of a sixth alternate embodiment of the present invention. The embodiment of FIG. 7U is similar to the embodiment of FIG. 7I, except that the antenna dielectric 116 is more uniform around the distal region of outer loop 112.

Figure 7X:
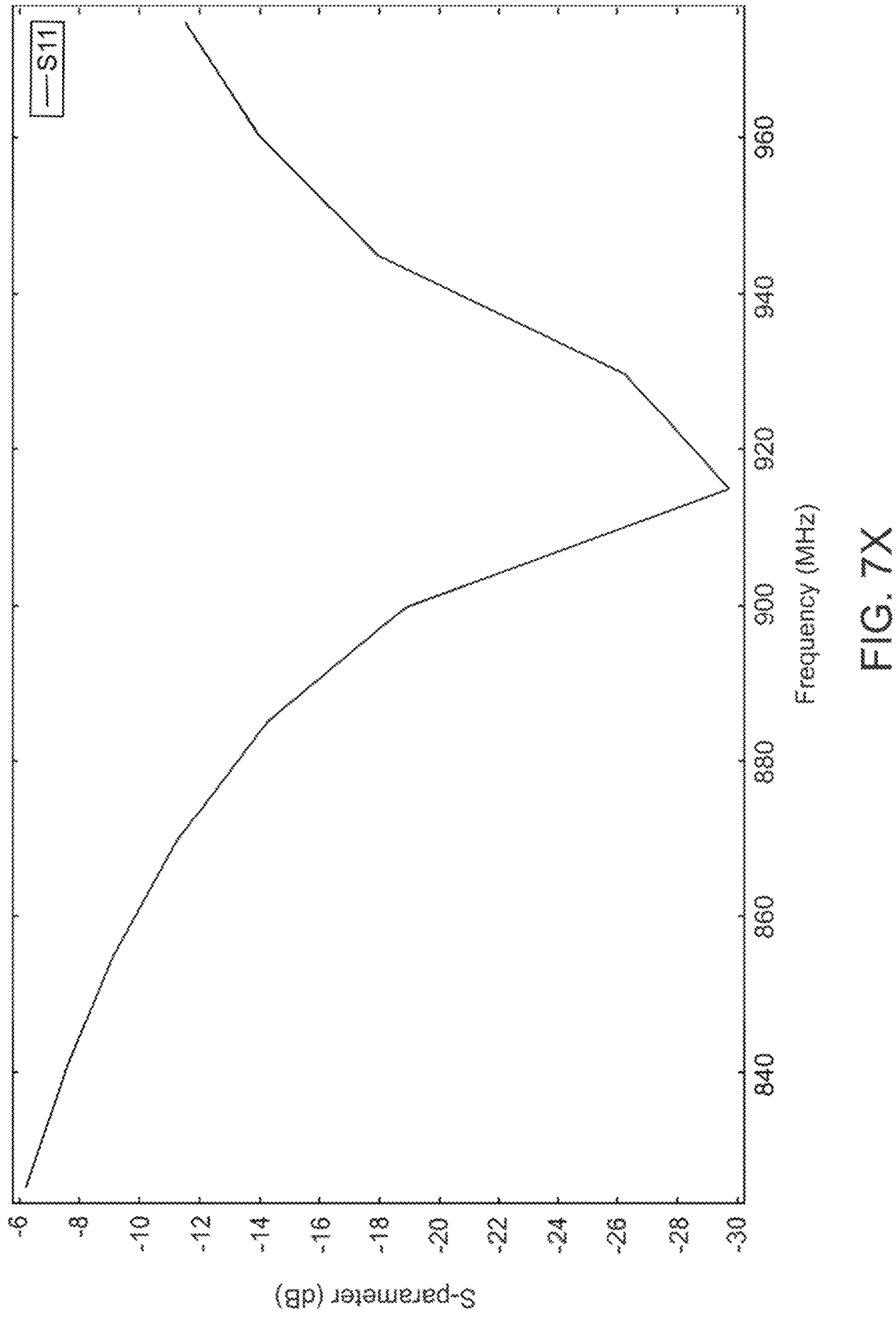

FIGS. 7V, 7W, and 7X show the electromagnetic field shape, location of hot spots, and the matching of the antenna of FIG. 7U. FIG. 7V shows that the electromagnetic field generated by the antenna of FIG. 7U has a roughly triangular shape that approximates the shape of the uterine cavity and is especially suited for endometrial ablation. FIG. 7W shows the location of the 100 degree Celsius zones. There is a large hot spot at the fundus and a smaller hot spot as shown. FIG. 7X shows good matching (about −29 dB) at 915 MHz frequency.

Figure 8A:
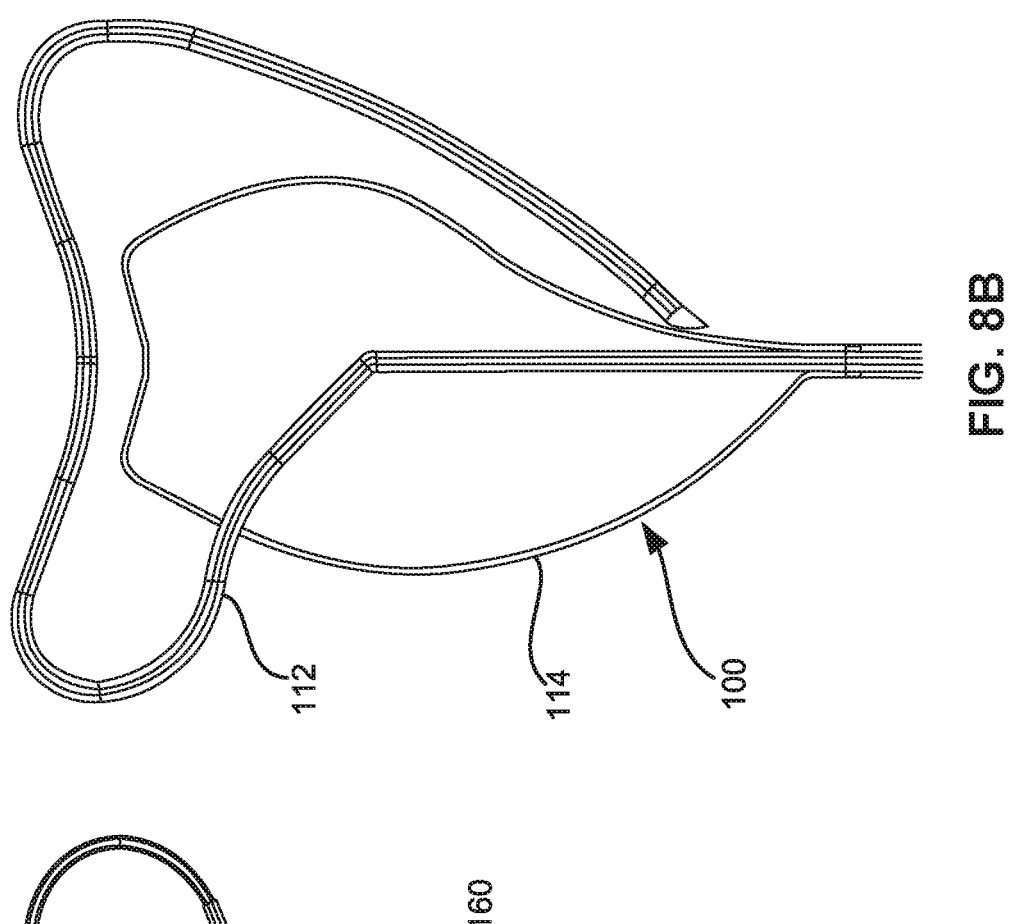
FIGS. 8A-8D show front views of additional variations of antennas.
Figure 8B:
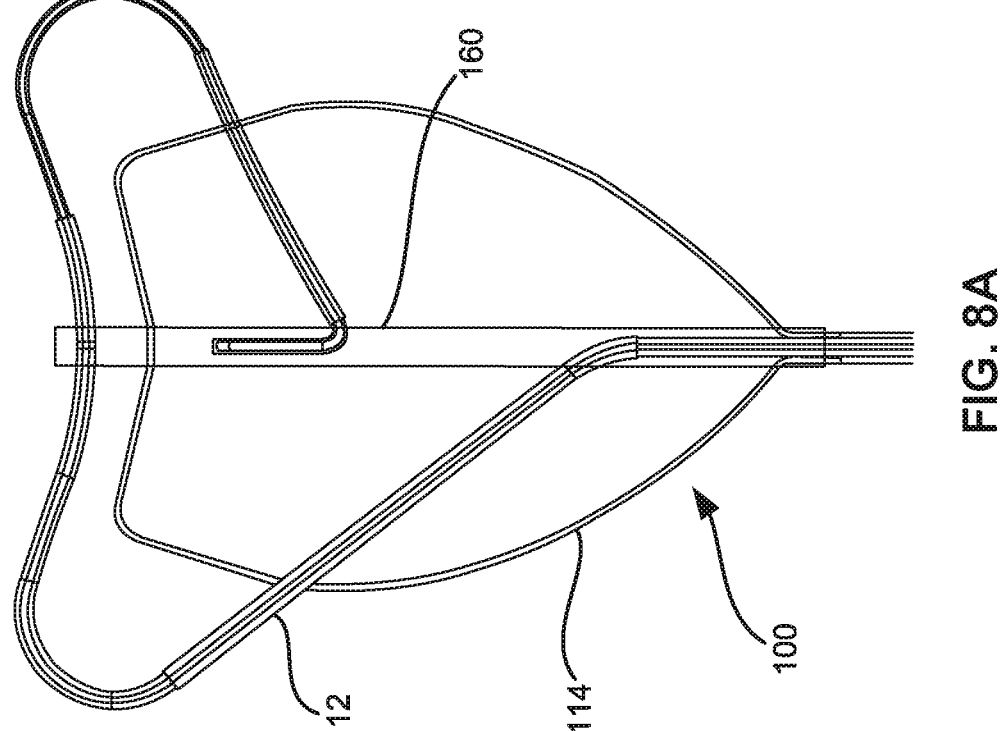
Figure 8D:
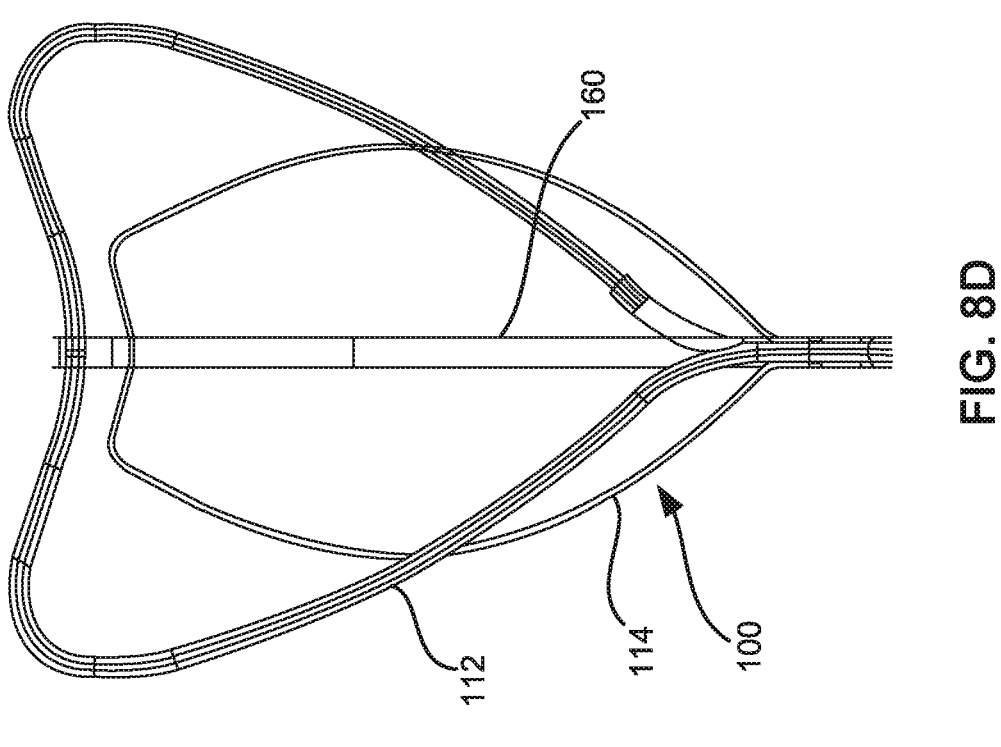
Figure 8C:
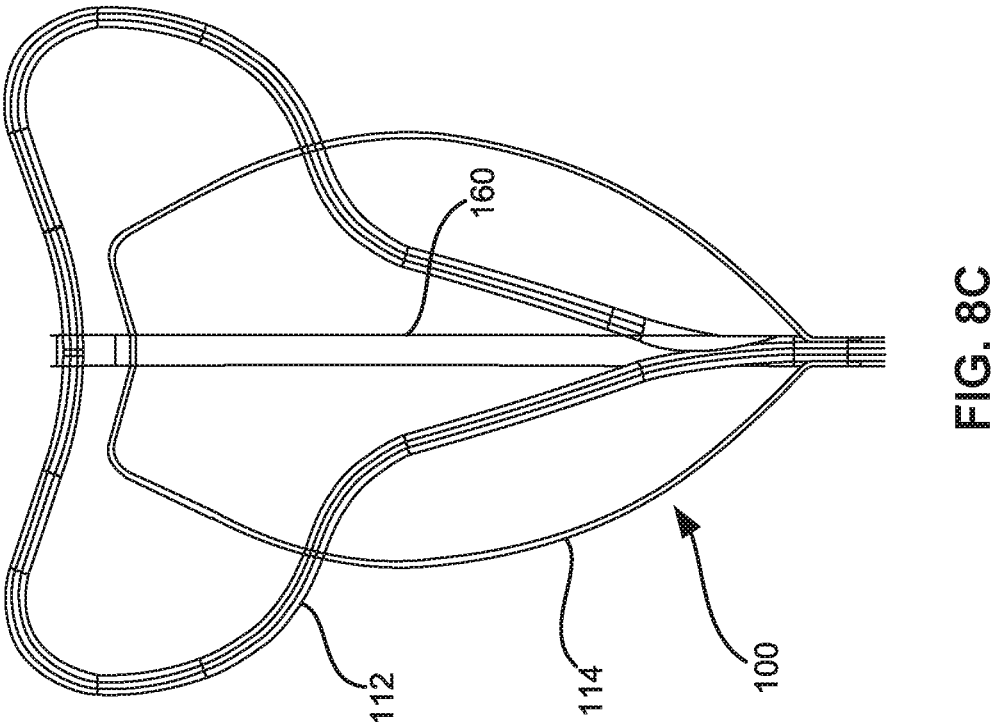

FIGS. 8A-8D show front views of four embodiments of the microwave antennas of the present invention. FIG. 8A shows an embodiment of antenna 104 with a general design as shown in FIG. 1A. However, in the embodiment shown in FIG. 8A, the design of antenna dielectrics 116 is different. Also, in the embodiment shown in FIG. 8A, the shape of center loop 114 is similar to the shape of center loop 114 of the embodiment of FIG. 1B. In the embodiment shown in FIG. 8B, the location, orientation, and the attachment of the distal end of outer loop 112 is different than in the embodiment of FIG. 1A. For example, the distal end of outer loop points in a proximal direction and is located close to the proximal end of antenna 104. Also, the shape of center loop 114 is non-symmetric as shown. For the sake of clarity, dielectric piece 160 or other structural elements are not shown in FIG. 8B. FIGS. 8C and 8D show embodiments wherein the location, orientation, and the attachment of the distal end of outer loop 112 is different than in the embodiment of FIG. 1A. For example, the distal end of outer loop points in a proximal direction and is located close to the proximal end of antenna 104. The distalmost region of outer loop 112 is also attached to a proximal region of antenna 104. Also, in the embodiments shown in FIGS. 8C and 8D, the shape of center loop 114 is similar to the shape of center loop 114 of the embodiment of FIG. 1B. Any of the microwave antennas 104 disclosed herein may be designed such that a portion of the antenna 104 is deployable by engaging a mechanical deployment system. The mechanical deployment system may be used to change antenna 104 from an insertion configuration to a working configuration capable of carrying out its intended purpose. One example of such a mechanical deployment system is a system of one or more pullable and releasable pull wires.

Any of the antennas 104 disclosed herein may comprise one or more mechanisms to ensure proper deployment of antenna 104 in the anatomy. In one such embodiment, the shape memory or super-elastic nature of one or both of one or more radiating elements 112 and one or more shaping elements 114 ensures proper deployment of antenna 104 in the anatomy. In one embodiment, one or more radiating elements 112 and/or one or more shaping elements 114 are embedded in a rigid or flexible antenna dielectric 116. Antenna dielectric 116 may be used to fix the relative positions of radiating elements 112 and shaping elements 114 thereby ensuring proper deployment in the anatomy. Such an antenna dielectric 116 may be substantially planar or substantially linear or substantially 3-dimensional. Such antenna dielectrics 116 may be one or more rigid or flexible struts or connection elements connecting one or more radiating elements 112 and one or more shaping elements 114. Such struts or connection elements fix the relative positions of radiating elements 112 and shaping elements 114 thereby ensuring proper deployment of antenna 104 in the anatomy. In one embodiment, a dielectric constraining element mechanically shapes antenna 104 and also shapes the microwave field profile of antenna 104.

Even though a majority of the disclosure uses a coaxial cable as an example of a transmission line, an alternate transmission lines for transmitting microwaves may be used. Examples of such alternate transmission lines for transmitting microwaves include, but are not limited to: waveguides, microstrip lines, strip lines, coplanar waveguides and rectax. In such embodiments, the shaping element(s) 114 may be electrically connected directly or indirectly to the shielding element of the transmission line. For example, in a strip line, wherein the shielding element is the combination of the two ground planes, shaping element(s) 114 may be electrically connected directly or indirectly to the combination of the two ground planes. For example, in a hollow metallic waveguide, wherein the shielding element is the electrically conducting wall, shaping element(s) 114 may be electrically connected directly or indirectly to the electrically conducting wall.

In one embodiment, microwave reflectometry is used to determine the proper positioning and/or proper deployment of antenna 104. Examples of such methods are disclosed in commonly assigned U.S. Pat. No. 9,462,642, the entire disclosure of which is incorporated by reference.

Several examples or embodiments of the devices and methods are discussed herein, but various modifications, additions and deletions may be made to those examples and embodiments without departing from the intended spirit and scope of the invention. Thus, any element, component, method step or attribute of one method or device embodiment may be incorporated into or used for another method or device embodiment, unless to do so would render the resulting method or device embodiment unsuitable for its intended use. For example, several embodiments of antennas 104 may be created by combining a device feature (e.g. radiating element 112) of one antenna embodiment with a device feature (e.g. shaping element 114) of another antenna embodiment unless to do so would render the resulting antenna embodiment unsuitable for its intended use. Any suitable antenna disclosed herein may be used to perform any of the methods disclosed herein. If the various steps of a method are disclosed in a particular order, the various steps may be carried out in any other order unless doing so would render the method embodiment unsuitable for its intended use. Various reasonable modifications, additions and deletions of the described examples or embodiments are to be considered equivalents of the described examples or embodiments.

Any of the generators disclosed herein may comprise one or more of: a processor, a memory, and a user interface for performing one or more of the method embodiments disclosed herein. The methods and systems described herein can be used in any region of the body and on any tissue or organ. Any of the generators disclosed herein may comprise one or more of: a processor, a memory, and a user interface.

We claim:

1. A medical device for treating tissue by applying a microwave energy from a transmission line coupled to a power supply, the medical device comprising:

an antenna comprising a radiating element, a shaping element and a dielectric piece;

the shaping element being electrically grounded using the power supply;

the dielectric piece having a distal end portion extending along a center of the antenna on a longitudinal axis of the antenna; and the radiating element having a first portion and a second portion, and a middle portion therebetween which collectively form a working profile, the radiating element configured to be constrained within a delivery device and to assume the working profile when unconstrained, where the radiating element is coupled to the dielectric piece, wherein the first portion and the second portion are coupled to the dielectric piece where the first portion and the second portion are spaced apart and extend in opposite directions longitudinally along the longitudinal axis, and where the distal end portion of the dielectric piece is directly coupled to the middle portion; and wherein application of microwave energy from the power supply to the antenna generates a microwave field.

2. The medical device of claim 1, where the working profile is planar.

3. The medical device of claim 1, where the working profile is non-planar.

4. The medical device of claim 1, wherein the first portion and second portion of the radiating element are linear.

5. The medical device of claim 1, wherein the middle portion is non-linear.

6. The medical device of claim 1, wherein at least one region of the middle portion extends transversely relative to the longitudinal axis.

7. The medical device of claim 6, wherein a portion of the shaping element is located adjacent to the radiating element, wherein a highest concentration of the microwave field is generated towards a distal end portion of the antenna.

8. The medical device of claim 6, wherein at least one region of the middle portion extends perpendicular to the longitudinal axis.

9. The medical device of claim 1, wherein the radiating element extends from a first location on the dielectric piece.

10. The medical device of claim 7, where the second portion of the radiating element extends from a second location on the dielectric piece.

11. The medical device of claim 1, wherein the middle portion is directly mechanically coupled to the dielectric piece.

12. The medical device of claim 11, where the dielectric piece has a stepped outer diameter.

13. The medical device of claim 1, wherein the radiating element is covered by at least a first dielectric covering.

14. The medical device of claim 13, wherein a thickness of the first dielectric covering varies on the radiating element.

15. The medical device of claim 13, wherein the first dielectric covering comprises a plurality of dielectric materials.

16. The medical device of claim 1, wherein the shaping element comprises an electrically conductive material.

17. The medical device of claim 16, wherein the shaping element is electrically connected to a shielding element of the transmission line.

18. The medical device of claim 1, wherein a bend angle by which the second portion is bent relative to the radiating element immediately proximal to the second portion is greater than ninety degrees.

19. The medical device of claim 1, wherein a distal end of the radiating element points in a distal direction.

20. The medical device of claim 1, wherein the first portion and the second portion are parallel to each other.

* * * * *